US008852181B2

(12) United States Patent
Malecki et al.

(10) Patent No.: US 8,852,181 B2
(45) Date of Patent: Oct. 7, 2014

(54) ENERGY BASED DEVICES AND METHODS FOR TREATMENT OF ANATOMIC TISSUE DEFECTS

(75) Inventors: William Malecki, San Francisco, CA (US); Dan Francis, Mountain View, CA (US); Kenneth Horne, Palo Alto, CA (US); Mark E. Deem, Mountain View, CA (US); Hanson Gifford, Woodside, CA (US); Jose Alejandro, Sunnyvale, CA (US)

(73) Assignee: Terumo Kabushiki Kaisha, Tokyo (JP)

( * ) Notice: Subject to any disclaimer, the term of this patent is extended or adjusted under 35 U.S.C. 154(b) by 1392 days.

(21) Appl. No.: 11/855,787

(22) Filed: Sep. 14, 2007

(65) Prior Publication Data

US 2008/0004658 A1 Jan. 3, 2008

Related U.S. Application Data

(63) Continuation of application No. 10/873,348, filed on Jun. 21, 2004, now Pat. No. 7,293,562, which is a continuation-in-part of application No. 10/679,245, filed on Oct. 2, 2003, now Pat. No. 6,939,348.

(60) Provisional application No. 60/490,082, filed on Jul. 24, 2003, provisional application No. 60/478,035, filed on Jun. 11, 2003, provisional application No. 60/458,854, filed on Mar. 27, 2003.

(51) Int. Cl.
*A61B 18/14* (2006.01)
*A61B 17/00* (2006.01)
*A61B 17/34* (2006.01)
*A61B 19/00* (2006.01)
*A61B 17/30* (2006.01)
*A61B 18/00* (2006.01)

(52) U.S. Cl.
CPC ......... *A61B 17/0057* (2013.01); *A61B 18/1445* (2013.01); *A61B 2017/00867* (2013.01);

(Continued)

(58) Field of Classification Search
USPC .................. 606/41, 48–50; 607/101, 102, 122
See application file for complete search history.

(56) References Cited

U.S. PATENT DOCUMENTS

| 2,275,167 A | 3/1942 | Bierman |
| 2,580,628 A | 1/1952 | Welsh |

(Continued)

FOREIGN PATENT DOCUMENTS

| EP | 135840 A2 | 4/1985 |
| EP | 199694 A2 | 10/1986 |

(Continued)

OTHER PUBLICATIONS

Anzola et al., "Potential Source of Cerebral Embolism in Migraine with Aura," *Neurology* (1999) 52(8): 1622.

(Continued)

*Primary Examiner* — Michael Peffley
(74) *Attorney, Agent, or Firm* — Oblon, Spivak, McClelland, Maier & Neustadt, L.L.P.

(57) ABSTRACT

Methods and apparatus for treatment of anatomic defects in human tissues, such as patent foramen ovale (PFO), atrial or ventricular septal defects, left atrial appendage, patent ductus arteriosis, blood vessel wall defects and certain electrophysiological defects, involve positioning a distal end of an elongate catheter device at the site of the anatomic defect, engaging tissues at the site of the anatomic defect to bring the tissues together, and applying energy to the tissues with the catheter device to substantially close the anatomic defect acutely. Apparatus generally includes an elongate catheter having a proximal end and a distal end, a vacuum application member coupled with the distal end for engaging tissues at the site of the anatomic defect and applying vacuum to the tissues to bring them together, and at least one energy transmission member coupled with the vacuum application member for applying energy to tissues at the site of the anatomic defect to substantially close the defect acutely.

18 Claims, 15 Drawing Sheets

(52) U.S. Cl.
CPC ..... *A61B 17/3439* (2013.01); *A61B 2019/5217* (2013.01); *C08L 2201/12* (2013.01); *A61B 2017/306* (2013.01); *A61B 2017/3445* (2013.01); *A61B 2018/00791* (2013.01); *A61B 2018/00875* (2013.01); *A61B 2018/00351* (2013.01); *A61B 2018/00619* (2013.01); *A61B 2018/00898* (2013.01); *A61B 18/1492* (2013.01); *A61B 2018/00261* (2013.01); *A61B 2018/00291* (2013.01); *A61B 2018/1472* (2013.01); *A61B 2017/00575* (2013.01); *A61B 2018/00702* (2013.01); *A61B 2018/0063* (2013.01); *A61B 2018/00285* (2013.01); *A61B 2018/00214* (2013.01)
USPC ............................................. 606/41; 607/122

(56) References Cited

U.S. PATENT DOCUMENTS

| | | |
|---|---|---|
| 2,888,928 A | 6/1959 | Seiger |
| 3,490,442 A | 1/1970 | Streu |
| 3,862,627 A | 1/1975 | Hans, Sr. |
| 3,874,388 A | 4/1975 | King et al. |
| 3,906,955 A | 9/1975 | Roberts |
| 4,307,720 A | 12/1981 | Weber, Jr. |
| 4,326,529 A | 4/1982 | Doss et al. |
| 4,473,077 A | 9/1984 | Noiles et al. |
| 4,485,817 A | 12/1984 | Swiggett |
| 4,532,924 A | 8/1985 | Auth et al. |
| 4,556,065 A | 12/1985 | Hoffmann |
| 4,562,838 A | 1/1986 | Walker |
| 4,590,934 A | 5/1986 | Malis et al. |
| 4,682,596 A | 7/1987 | Bales et al. |
| 4,788,975 A | 12/1988 | Shturman et al. |
| 4,798,594 A | 1/1989 | Hillstead |
| 4,832,048 A | 5/1989 | Cohen |
| 4,884,567 A | 12/1989 | Elliott et al. |
| 4,895,565 A | 1/1990 | Hillstead |
| 4,911,159 A | 3/1990 | Johnson et al. |
| 4,919,129 A | 4/1990 | Weber, Jr. et al. |
| 4,929,246 A | 5/1990 | Sinofsky |
| 4,976,711 A | 12/1990 | Parins et al. |
| 4,986,889 A | 1/1991 | Charamathieu et al. |
| 5,041,095 A | 8/1991 | Littrell |
| 5,042,707 A | 8/1991 | Taheri |
| 5,055,100 A | 10/1991 | Olsen |
| 5,056,517 A | 10/1991 | Fenici |
| 5,057,107 A | 10/1991 | Parins et al. |
| 5,071,417 A | 12/1991 | Sinofsky |
| 5,071,418 A | 12/1991 | Rosenbaum |
| 5,078,717 A | 1/1992 | Parins et al. |
| 5,099,827 A | 3/1992 | Melzer et al. |
| RE33,925 E | 5/1992 | Bales et al. |
| 5,125,928 A | 6/1992 | Parins et al. |
| 5,156,608 A | 10/1992 | Troidl et al. |
| 5,156,613 A | 10/1992 | Sawyer |
| 5,171,311 A | 12/1992 | Rydell |
| 5,195,959 A | 3/1993 | Smith |
| 5,196,007 A | 3/1993 | Ellman et al. |
| 5,197,963 A | 3/1993 | Parins |
| 5,207,670 A | 5/1993 | Sinofsky |
| 5,209,756 A | 5/1993 | Seedhom et al. |
| 5,290,278 A | 3/1994 | Anderson |
| 5,292,362 A | 3/1994 | Bass et al. |
| 5,295,955 A | 3/1994 | Rosen et al. |
| 5,300,065 A | 4/1994 | Anderson |
| 5,336,221 A | 8/1994 | Anderson |
| 5,336,252 A | 8/1994 | Cohen |
| 5,342,413 A | 8/1994 | Hirschberg et al. |
| 5,345,935 A | 9/1994 | Hirsch |
| 5,370,675 A | 12/1994 | Edwards et al. |
| 5,380,304 A | 1/1995 | Parker |
| 5,383,917 A | 1/1995 | Desai et al. |
| 5,405,322 A | 4/1995 | Lennox et al. |
| 5,409,479 A | 4/1995 | Dew et al. |
| 5,409,481 A | 4/1995 | Poppas et al. |
| 5,500,012 A | 3/1996 | Brucker et al. |
| 5,505,730 A | 4/1996 | Edwards |
| 5,507,744 A | 4/1996 | Tay et al. |
| 5,540,677 A | 7/1996 | Sinofsky |
| 5,569,239 A | 10/1996 | Sinofsky |
| 5,571,216 A | 11/1996 | Anderson |
| 5,575,772 A | 11/1996 | Lennox |
| 5,584,872 A | 12/1996 | Lafontaine et al. |
| 5,611,794 A | 3/1997 | Sauer et al. |
| 5,620,481 A | 4/1997 | Desai et al. |
| 5,626,607 A | 5/1997 | Malecki et al. |
| 5,662,643 A | 9/1997 | Kung et al. |
| 5,665,109 A | 9/1997 | Yoon |
| 5,669,934 A | 9/1997 | Sawyer |
| 5,687,723 A * | 11/1997 | Avitall .......................... 600/374 |
| 5,693,078 A | 12/1997 | Desai et al. |
| 5,709,224 A | 1/1998 | Behl |
| 5,713,891 A | 2/1998 | Poppas |
| 5,725,522 A | 3/1998 | Sinofsky |
| 5,730,742 A | 3/1998 | Wojciechowicz |
| 5,749,895 A | 5/1998 | Sawyer et al. |
| 5,782,899 A | 7/1998 | Imran |
| 5,814,065 A | 9/1998 | Diaz |
| 5,824,015 A | 10/1998 | Sawyer |
| 5,827,265 A | 10/1998 | Glinsky et al. |
| 5,846,196 A | 12/1998 | Siekmeyer et al. |
| 5,855,312 A | 1/1999 | Toledano |
| 5,871,443 A | 2/1999 | Edwards et al. |
| 5,919,200 A | 7/1999 | Stambaugh et al. |
| 5,925,078 A | 7/1999 | Anderson |
| 5,928,266 A | 7/1999 | Kontos |
| 5,931,165 A | 8/1999 | Reich et al. |
| 5,944,738 A | 8/1999 | Amplatz et al. |
| 5,971,983 A * | 10/1999 | Lesh .............................. 606/41 |
| 5,972,023 A | 10/1999 | Tanner et al. |
| 5,972,024 A | 10/1999 | Northrup, III et al. |
| 6,004,316 A | 12/1999 | Laufer |
| 6,012,457 A | 1/2000 | Lesh |
| 6,036,699 A | 3/2000 | Andreas et al. |
| 6,050,994 A | 4/2000 | Sherman |
| 6,056,760 A | 5/2000 | Koike et al. |
| 6,063,081 A | 5/2000 | Mulier |
| 6,063,085 A | 5/2000 | Tay |
| 6,083,223 A | 7/2000 | Baker |
| 6,086,570 A | 7/2000 | Aboul-Hosn et al. |
| 6,086,586 A | 7/2000 | Hooven |
| 6,087,552 A | 7/2000 | Gregory |
| 6,092,528 A | 7/2000 | Edwards |
| 6,132,429 A | 10/2000 | Baker |
| 6,149,660 A | 11/2000 | Laufer et al. |
| 6,156,032 A | 12/2000 | Lennox |
| 6,168,594 B1 | 1/2001 | Lafontaine |
| 6,211,335 B1 | 4/2001 | Owen et al. |
| 6,221,068 B1 | 4/2001 | Fried et al. |
| 6,236,875 B1 | 5/2001 | Bucholz |
| 6,248,124 B1 | 6/2001 | Pedros et al. |
| 6,257,241 B1 | 7/2001 | Wampler |
| 6,290,674 B1 | 9/2001 | Roue et al. |
| 6,302,898 B1 | 10/2001 | Edwards et al. |
| 6,323,037 B1 | 11/2001 | Lauto et al. |
| 6,325,798 B1 | 12/2001 | Edwards et al. |
| 6,355,030 B1 | 3/2002 | Aldrich et al. |
| 6,358,246 B1 | 3/2002 | Behl et al. |
| 6,375,668 B1 | 4/2002 | Gifford et al. |
| 6,383,198 B1 | 5/2002 | Hamilton |
| 6,391,048 B1 | 5/2002 | Ginn et al. |
| 6,391,049 B1 | 5/2002 | McNally et al. |
| 6,398,779 B1 | 6/2002 | Buysse et al. |
| 6,398,782 B1 | 6/2002 | Pecor et al. |
| 6,398,797 B2 | 6/2002 | Bombard et al. |
| 6,401,720 B1 | 6/2002 | Stevens et al. |
| 6,409,720 B1 | 6/2002 | Hissong et al. |
| 6,413,254 B1 | 7/2002 | Hissong et al. |
| 6,419,669 B1 | 7/2002 | Frazier et al. |
| 6,423,057 B1 | 7/2002 | He et al. |
| 6,436,088 B2 | 8/2002 | Frazier et al. |
| 6,451,013 B1 | 9/2002 | Bays et al. |
| 6,456,865 B2 | 9/2002 | Samson |

(56) References Cited

U.S. PATENT DOCUMENTS

| | | |
|---|---|---|
| 6,458,100 B2 | 10/2002 | Roue et al. |
| 6,475,213 B1 | 11/2002 | Whayne et al. |
| 6,482,224 B1 | 11/2002 | Michler et al. |
| 6,514,250 B1 | 2/2003 | Jahns et al. |
| 6,529,756 B1 * | 3/2003 | Phan et al. ............... 600/374 |
| 6,558,314 B1 | 5/2003 | Adelman et al. |
| 6,558,382 B2 | 5/2003 | Jahns et al. |
| 6,562,037 B2 | 5/2003 | Paton et al. |
| 6,583,117 B2 | 6/2003 | Owen et al. |
| 6,584,360 B2 | 6/2003 | Francischelli et al. |
| 6,589,237 B2 | 7/2003 | Woloszko |
| 6,606,523 B1 | 8/2003 | Jenkins |
| 6,641,604 B1 | 11/2003 | Adelman |
| 6,645,202 B1 | 11/2003 | Pless et al. |
| 6,645,225 B1 | 11/2003 | Atkinson |
| 6,648,897 B2 | 11/2003 | Hamilton |
| 6,652,518 B2 | 11/2003 | Wellman et al. |
| 6,669,693 B2 | 12/2003 | Friedman |
| 6,676,685 B2 | 1/2004 | Pedros et al. |
| 6,682,546 B2 | 1/2004 | Amplatz |
| 6,692,450 B1 | 2/2004 | Coleman |
| 6,702,835 B2 | 3/2004 | Ginn |
| 6,712,804 B2 | 3/2004 | Roue et al. |
| 6,712,836 B1 | 3/2004 | Berg et al. |
| 6,716,211 B2 | 4/2004 | Mulier et al. |
| 6,726,718 B1 | 4/2004 | Carlyle et al. |
| 6,730,108 B2 | 5/2004 | Van Tassel et al. |
| 6,733,498 B2 | 5/2004 | Paton et al. |
| 6,736,810 B2 | 5/2004 | Hoey et al. |
| 6,755,790 B2 | 6/2004 | Stewart et al. |
| 6,770,072 B1 | 8/2004 | Truckai et al. |
| 6,776,784 B2 | 8/2004 | Ginn |
| 6,790,218 B2 | 9/2004 | Jayaraman |
| 6,846,319 B2 | 1/2005 | Ginn et al. |
| 6,887,238 B2 | 5/2005 | Jahns |
| 6,893,431 B2 | 5/2005 | Naimark et al. |
| 6,893,442 B2 | 5/2005 | Whayne |
| 6,918,908 B2 | 7/2005 | Bonner et al. |
| 6,926,716 B2 | 8/2005 | Baker et al. |
| 6,929,644 B2 | 8/2005 | Truckai et al. |
| 6,932,812 B2 | 8/2005 | Crowley et al. |
| 6,939,348 B2 | 9/2005 | Malecki et al. |
| 6,946,134 B1 | 9/2005 | Rosen et al. |
| 6,960,205 B2 | 11/2005 | Jahns et al. |
| 7,025,756 B2 | 4/2006 | Frazier et al. |
| 7,094,215 B2 | 8/2006 | Davison et al. |
| 7,165,552 B2 | 1/2007 | Deem et al. |
| 7,186,251 B2 | 3/2007 | Malecki et al. |
| 7,238,182 B2 | 7/2007 | Swoyer et al. |
| 7,293,562 B2 | 11/2007 | Malecki et al. |
| 7,311,701 B2 | 12/2007 | Gifford et al. |
| 2001/0020166 A1 | 9/2001 | Daly et al. |
| 2001/0037129 A1 | 11/2001 | Thill |
| 2001/0051803 A1 | 12/2001 | Desai et al. |
| 2002/0128672 A1 | 9/2002 | Dinger et al. |
| 2002/0143322 A1 | 10/2002 | Haghighi |
| 2002/0156472 A1 | 10/2002 | Lee et al. |
| 2003/0028189 A1 | 2/2003 | Woloszko et al. |
| 2003/0045893 A1 | 3/2003 | Ginn |
| 2003/0045901 A1 | 3/2003 | Opolski |
| 2003/0050665 A1 | 3/2003 | Ginn |
| 2003/0065364 A1 | 4/2003 | Wellman et al. |
| 2003/0069570 A1 | 4/2003 | Witzel |
| 2003/0078578 A1 | 4/2003 | Truckai et al. |
| 2003/0092988 A1 | 5/2003 | Makin |
| 2003/0093071 A1 | 5/2003 | Hauck et al. |
| 2003/0120268 A1 | 6/2003 | Bertolero et al. |
| 2003/0144652 A1 | 7/2003 | Baker et al. |
| 2003/0144694 A1 | 7/2003 | Chanduszko et al. |
| 2003/0158551 A1 | 8/2003 | Paton et al. |
| 2003/0199868 A1 | 10/2003 | Desai et al. |
| 2003/0208232 A1 | 11/2003 | Blaeser |
| 2003/0225421 A1 | 12/2003 | Peavey et al. |
| 2003/0233091 A1 | 12/2003 | Whayne et al. |
| 2004/0059347 A1 | 3/2004 | Hamilton |
| 2004/0092973 A1 | 5/2004 | Chanduszko et al. |
| 2004/0098031 A1 | 5/2004 | Van der Burg et al. |
| 2004/0098042 A1 | 5/2004 | Devellian et al. |
| 2004/0102721 A1 | 5/2004 | Mckinley |
| 2004/0143292 A1 | 7/2004 | Marino et al. |
| 2004/0153057 A1 | 8/2004 | Davison |
| 2004/0153098 A1 | 8/2004 | Chin et al. |
| 2004/0176799 A1 | 9/2004 | Chanduszko et al. |
| 2004/0220596 A1 | 11/2004 | Frazier et al. |
| 2004/0243122 A1 | 12/2004 | Auth |
| 2004/0249398 A1 | 12/2004 | Ginn |
| 2005/0021059 A1 | 1/2005 | Cole et al. |
| 2005/0033288 A1 | 2/2005 | Auth et al. |
| 2005/0033327 A1 | 2/2005 | Gainor et al. |
| 2005/0055050 A1 | 3/2005 | Alfaro |
| 2005/0065506 A1 | 3/2005 | Phan |
| 2005/0065509 A1 | 3/2005 | Coldwell et al. |
| 2005/0070923 A1 | 3/2005 | Mcintosh |
| 2005/0075665 A1 | 4/2005 | Brenzel et al. |
| 2005/0119675 A1 | 6/2005 | Adams et al. |
| 2005/0125032 A1 | 6/2005 | Whisenant et al. |
| 2005/0171526 A1 | 8/2005 | Rioux et al. |
| 2005/0187568 A1 | 8/2005 | Klenk et al. |
| 2005/0192626 A1 | 9/2005 | Widomski et al. |
| 2005/0192627 A1 | 9/2005 | Whisenant et al. |
| 2005/0192654 A1 | 9/2005 | Chanduszko et al. |
| 2005/0209636 A1 | 9/2005 | Widomski et al. |
| 2005/0216054 A1 | 9/2005 | Widomski et al. |
| 2005/0251201 A1 | 11/2005 | Roue et al. |
| 2005/0256532 A1 | 11/2005 | Nayak et al. |
| 2005/0267495 A1 | 12/2005 | Ginn et al. |
| 2005/0267525 A1 | 12/2005 | Chanduszko |
| 2006/0009762 A1 | 1/2006 | Whayne |
| 2006/0027241 A1 | 2/2006 | Malecki et al. |
| 2006/0036284 A1 | 2/2006 | Blaeser et al. |
| 2006/0052821 A1 | 3/2006 | Abbott et al. |
| 2006/0069408 A1 | 3/2006 | Kato |
| 2006/0079870 A1 | 4/2006 | Barry |
| 2006/0079887 A1 | 4/2006 | Buysse et al. |
| 2006/0173510 A1 | 8/2006 | Besio et al. |
| 2006/0241581 A1 | 10/2006 | Malecki et al. |
| 2006/0241582 A1 | 10/2006 | Malecki et al. |
| 2006/0241583 A1 | 10/2006 | Malecki et al. |
| 2006/0241584 A1 | 10/2006 | Malecki et al. |
| 2006/0247612 A1 | 11/2006 | Malecki et al. |
| 2006/0276779 A1 | 12/2006 | Malecki et al. |
| 2007/0010806 A1 | 1/2007 | Malecki et al. |
| 2007/0078485 A1 | 4/2007 | Deem et al. |
| 2007/0088355 A9 | 4/2007 | Auth |
| 2007/0123851 A1 | 5/2007 | Alejandro et al. |
| 2007/0123852 A1 | 5/2007 | Deem et al. |
| 2007/0299434 A1 | 12/2007 | Malecki et al. |
| 2008/0004658 A1 | 1/2008 | Malecki et al. |
| 2008/0140113 A1 | 6/2008 | Taimisto et al. |

FOREIGN PATENT DOCUMENTS

| | | |
|---|---|---|
| EP | 0265532 A1 | 5/1988 |
| EP | 0375556 A1 | 6/1990 |
| EP | 0428812 A1 | 5/1991 |
| EP | 0947165 A1 | 10/1999 |
| GB | 1260919 | 1/1972 |
| GB | 1550676 | 8/1979 |
| GB | 2 359 024 A | 8/2001 |
| WO | WO 85/00018 A1 | 1/1985 |
| WO | WO 87/04081 A1 | 7/1987 |
| WO | WO 90/04352 A1 | 5/1990 |
| WO | WO 91/15996 A1 | 10/1991 |
| WO | WO 92/04864 A1 | 4/1992 |
| WO | WO 93/05705 A1 | 4/1993 |
| WO | WO 93/15791 A1 | 8/1993 |
| WO | WO 94/00178 A1 | 1/1994 |
| WO | WO 98/07375 A1 | 2/1998 |
| WO | WO 99/18862 A1 | 4/1999 |
| WO | WO 99/18864 A1 | 4/1999 |
| WO | WO 99/18870 A1 | 4/1999 |
| WO | WO 99/18871 A1 | 4/1999 |
| WO | WO 99/23959 A1 | 5/1999 |
| WO | WO 99/49788 A | 10/1999 |

(56) References Cited

FOREIGN PATENT DOCUMENTS

| | | |
|---|---|---|
| WO | WO 00/07506 A2 | 2/2000 |
| WO | WO 00/09027 A1 | 2/2000 |
| WO | WO 01/13810 A1 | 3/2001 |
| WO | WO 01/78596 A1 | 10/2001 |
| WO | WO 01/82778 A | 11/2001 |
| WO | WO 03/022159 A1 | 3/2003 |
| WO | WO 03/022160 A1 | 3/2003 |
| WO | WO 03/026496 A2 | 4/2003 |
| WO | WO 03/053493 A2 | 7/2003 |
| WO | WO 03/071957 A2 | 9/2003 |
| WO | WO 03/082076 A2 | 10/2003 |
| WO | WO 03/094742 A1 | 11/2003 |
| WO | WO 2004/019791 A2 | 3/2004 |
| WO | WO 2004/043266 A2 | 5/2004 |
| WO | WO 2004/069055 A2 | 8/2004 |
| WO | WO 2004/082532 A1 | 9/2004 |
| WO | WO 2004/091411 A2 | 10/2004 |
| WO | WO 2005/006990 A2 | 1/2005 |
| WO | WO 2005/027753 A1 | 3/2005 |
| WO | WO 2005/034738 A2 | 4/2005 |
| WO | WO 2005/074814 A2 | 8/2005 |
| WO | WO 2005/046487 A1 | 12/2005 |
| WO | WO 2005/115256 A | 12/2005 |

OTHER PUBLICATIONS

Athiraman et al., "Selective Photothermal Tissue Interaction Using 805-nm Laser and Indocyanine Green in Tissue Welding," *Journal of X-Ray Science and Technology*, vol. 12, No. 2, (2004), pp. 117-126.
Besio et al., "Quantizing the Depth of Bioelectrical Sources for Non-Invasive 3D Imaging," IJBEM, vol. 7, No. 2, (2005), 4 pages total.
De Castro et al., "Morphological and Functional Characteristics of Patent Foramen Ovale and Their Embolic Implications," *Stroke* (Oct. 2002), pp. 2407-2413.
Cordis Corporation, Cordis Ducor® Lumeleo™ Electorode Catheters [brochure], Cordis Corporation, (Dec. 1984), 2 pages.
Del Sette, "Migraine with Aura and Right-to-Left Shunt on Transcranial Doppler: A Case Control Study," *Cerebrovas Dis* (1998) 8:327-330.
Fenner et al., "Shear Strength of Tissue Bonds as a Function of Bonding Temperature: A Proposed Mechanism for Laser-Assisted Tissue Welding," *Lasers in Medical Science*, vol. 7, (1992), pp. 39-43.
Godlewski et al., "Applications and Mechanisms of Laser Tissue Welding in 1995: Review," *Proc. SPIE*, vol. 2623, (Jan. 1996) pp. 334-341.
Gillette, "Catheter Ablation in Dysrhythmias," *Cardio*, (Mar. 1984), pp. 67-69.
Ho et al., "Morphological Features Pertinent to Interventional Closure of Patent Oval Foramen," *J Interventional Cardiology*, vol. 16 No. 1, (2003), pp. 33-34.
Kennedy et al., "High-burst-Strength, feedback-controlled bipolar vessel sealing," *Surg Endosc* (1998) 12:876-878.
Koenig et al., "Role of Intracardiac Echocardiographic Guidance in Transcatheter Closure of Atrial Septal Defects and Patent Foramen Ovale Using the Amplatzer® Device," *J. Interventional Cardiology*, (2003) 16 (1): 51-62.
Morady, "Transvenous Catheter Ablation of a Posterospetial Accessory Pathway in a Patient with the Wolff Parkinson-White Syndrome," *The New England Journal of Medicine*, (Mar. 15, 1984), 310(11): 705-707.
Morandi et al., "Transcatheter Closure of Patent Foramen Ovale: A New Migraine Treatment?" *J Interventional Cardiology*, (2003), 16(1): 39-42.
Olson et al., "Developing an Animal Model for the Study of Fusion Using RF Energy," *Proc. SPIE*, vol. 5312, (2004), pp. 147-161.
Ott et al., "Comparative in Vitro Study of Tissue Welding Using a 808 nm Diode Laser and a Ho:YAG laser," *Lasers Med Sci*, vol. 16, (2001) pp. 260-266.
Pfleger, "Haemodynamic Quantification of Different Provocation Manoeuvres by Simultaneous Measurement of Right and Left Atrial Pressure: Implications for the Echocardiographic Detection of Persistent Foramen Ovale," *Eur J Echocardiography* (2001) 2: 88-93.
Polgar et al., "A New Technique for Closed-Chest Human His Bundle Ablation Using Suction Electrode Catheter and DC Shock," In: Perez Gomez F, ed. Cardiac Pacing Electrophysiology Tachyarrhythmias. Madrid, Spain: Grouz Publishers; 1985:1582-1586.
Polgar et al., "Comparison of Two Different Techniques for Closed-Chest His Bundle Ablation," *In: Perez Gomez F*, ed. Cardiac Pacing Electrophysiology Tachyarrhythmias. Madrid, Spain: Grouz Publishers; 1985:1578-1587.
Polgar, "Closed Chested Ablation of His Bundle: A New Technique Using Suction Electorde Catheter and DC Shock," *Nachdruck Aus: Cardio Pacing*, (1983), pp. 883-890.
Poppas et al., "Temperature-Controlled Laser Photocoagulation of Soft Tissue: in Vivo Evaluation Using a Tissue Welding Model," Lasers Surg Med., vol. 18, No. 4, (1996), pp. 335-344.
Stewart et al., "Laser Assisted Vascular Welding with Real Time Temperature Control," Lasers Surg Med., vol. 19, No. 1, (1996), pp. 9-16.
Stuart, "What's All the Flap About PFO Closure?," *Start-Up: Windhover's Review of Emerging Medical Ventures*, (Nov. 10, 2004), pp. 9-14.
Sztajzel et al., "Patent Foramen Ovale, a Possible Cause of Symptomatic Migraine: A Study of 74 Patients with Acute Ischemic Stroke," *Cerebrovas Dis* (2002) 13: 102-106.
Tang et al., "Quantitative Changes in Collagen Levels Following 830-nm Diode Laser Welding," Lasers Surg Med., vol. 22, No. 4, (1998), pp. 207-211.
Tang et al, "Morphologic Changes in Collagen Fibers after 830 nm Diode Laser Welding," Lasers Surg Med., vol. 21, No. 5 (1997), pp. 438-443.
Thomas, "Patent Foramen Ovale with Right-to-left Shunting: Echocariographic Alternatives," *Eur J Echocariography* (2001) 2:74-75.
Wilmhurst et al., "Effect on Migraine of Closure of Cardiac Right-to-Left Shunts to Prevent Recurrence of Decompression Illness of Illness or Stroke or for Haemodynamic Reasons," *The Lancet*, vol. 356, (Nov. 11, 2000), pp. 1648-1651.
Wilmhurst et al., "Relationship between Migraine and Cardiac and Pulmonary Right to Left Shunts," *Clinical Science* (2001) 100:215-220.
Canadian Office Action issued on Mar. 8, 2011 in corresponding Canadian Application No. 2,519,559.
European Search Report issued Nov. 24, 2010, in Patent Application No. 04758520.3.
U.S. Appl. No. 95/000,260, filed Jun. 22, 2007, Malecki et al.
U.S. Appl. No. 95/000,264, filed Jun. 18, 2007, Malecki et al.
European Office Action issued Mar. 11, 2011, in Patent Application No. 04 758 520.3.
Office Action issued Jan. 15, 2013 in Canadian Patent Application No. 2,519,559.
Office Action issued Sep. 9, 2013 in Canadian Patent Application No. 2,519,559.

\* cited by examiner

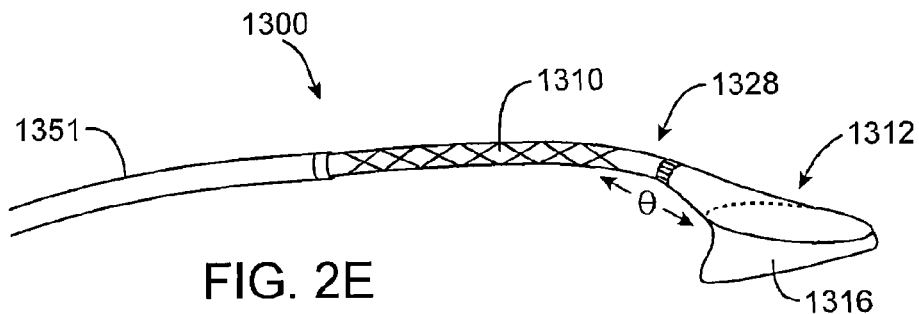
FIG. 2E
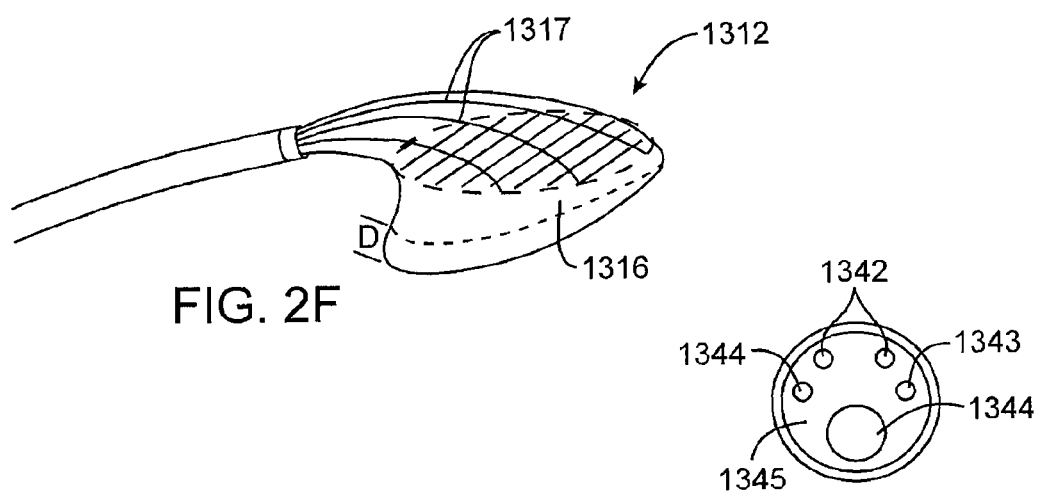
FIG. 2F
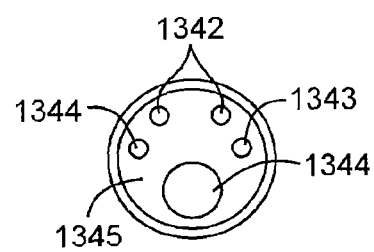
FIG. 2G"A
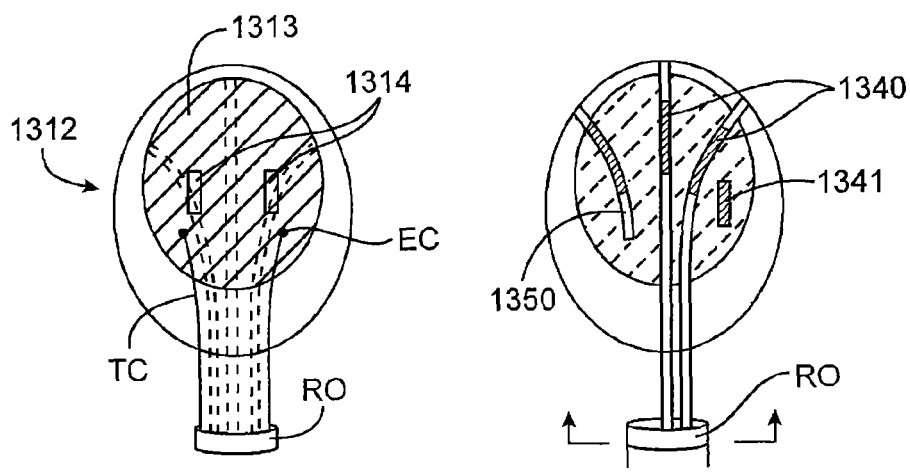
FIG. 2G'          FIG. 2G"

ENERGY BASED DEVICES AND METHODS FOR TREATMENT OF ANATOMIC TISSUE DEFECTS

CROSS-REFERENCES TO RELATED APPLICATIONS

This application is a continuation of U.S. application Ser. No. 10/873,348, now U.S. Pat. No. 7,293,562, filed on Jun. 21, 2004, which is a continuation in part of U.S. patent application Ser. No. 10/679,245, now U.S. Pat. No. 6,939,348, filed Oct. 2, 2003, and which claims priority to U.S. Provisional Patent Application Nos. 60/458,854, filed on Mar. 27, 2003; 60/478,035, filed on Jun. 11, 2003, and 60/490,082, filed on Jul. 24, 2003, the full disclosures of which are incorporated herein by reference.

BACKGROUND OF THE INVENTION

The invention generally relates to medical devices and methods. More specifically, the invention relates to energy based devices and methods for treatment of anatomic defects in human tissue, such as patent foramen ovale (PFO), atrial septal defect (ASD), ventricular septal defect (VSD), patent ductus arteriosis (PDA), left atrial appendages (LAA), blood vessel wall defects and certain electrophysiological defects.

The following is an example of how one particular type of anatomical defect—a PFO—is formed. Fetal blood circulation is very different from adult circulation. Because fetal blood is oxygenated by the placenta, rather than the fetal lungs, blood is generally shunted past the lungs to the peripheral tissues through a number of vessels and foramens that remain patent (i.e., open) during fetal life and typically close shortly after birth. For example, fetal blood passes directly from the right atrium through the foramen ovale into the left atrium, and a portion of blood circulating through the pulmonary artery trunk passes through the ductus arteriosus to the aorta. This fetal circulation is shown in attached FIG. 1.

At birth, as a newborn begins breathing, blood pressure in the left atrium rises above the pressure in the right atrium. In most newborns, a flap of tissue closes the foramen ovale and it heals together. In approximately 20,000 babies born each year in the US, the flap of tissue is missing, and the hole remains open as an atrial septal defect (ASD). In a much more significant percentage of the population (estimates range from 5% to 20% of the entire population), the flap is present but does not heal together. This condition is known as a patent foramen ovale (PFO). Whenever the pressure in the right atrium rises above that in the left atrium, blood pressure can push this patent channel open, allowing blood to flow from the right atrium to the left atrium. A patent ductus arteriosis (PDA) is a tubular communication between the pulmonary artery and the aorta, which typically closes shortly after birth.

Patent foramen ovale has long been considered a relatively benign condition, since it typically has little effect on the body's circulation. More recently, however, it has been found that a significant number of strokes may be caused at least in part by PFOs. In some cases, a stroke may occur because a PFO allows blood containing small thrombi to flow directly from the venous circulation to the arterial circulation and into the brain, rather than flowing to the lungs where the thrombi can become trapped and gradually dissolved. In other cases, a thrombus might form in the patent channel of the PFO itself and become dislodged when the pressures cause blood to flow from the right atrium to the left atrium. It has been estimated that patients with PFOs who have already had cryptogenic strokes may have a risk of having another stroke.

Further research is currently being conducted into the link between PFO and stroke. At the present time, if someone with a PFO has two or more strokes, the healthcare system in the U.S. may reimburse a surgical or other interventional procedure to definitively close the PFO. It is likely, however, that a more prophylactic approach would be warranted to close PFOs to prevent the prospective occurrence of a stroke. The cost and potential side-effects and complications of such a procedure must be low, however, since the event rate due to PFOs is relatively low. In younger patients, for example, PFOs sometimes close by themselves over time without any adverse health effects.

Another highly prevalent and debilitating condition—chronic migraine headache—has also been linked with PFO. Although the exact link has not yet been explained, PFO closure has been shown to eliminate or significantly reduce migraine headaches in many patients. Again, prophylactic PFO closure to treat chronic migraine headaches might be warranted if a relatively non-invasive procedure were available.

Currently available interventional therapies for defect closure are generally fairly invasive and/or have potential drawbacks. One strategy is simply to close a defect during open heart surgery for another purpose, such as heart valve surgery. This can typically be achieved via a simple procedure such as placing a stitch or two across the defect with vascular suture. Performing open heart surgery purely to close an asymptomatic PFO or even a very small ASD, however, would be very hard to justify.

A number of interventional devices for closing defects percutaneously have also been proposed and developed. Most of these devices are the same as or similar to ASD closure devices. They are typically "clamshell" or "double umbrella" shaped devices which deploy an area of biocompatible metal mesh or fabric (ePTFE or Dacron, for example) on each side of the atrial septum, held together with a central axial element, to cover the defect. This umbrella then heals into the atrial septum, with the healing response forming a uniform layer of tissue or "pannus" over the device. Such devices have been developed, for example, by companies such as Nitinol Medical Technologies, Inc. (Boston, Mass.) and AGA Medical, Inc. (White Bear Lake, Minn.). U.S. Pat. No. 6,401,720 describes a method and apparatus for thoracoscopic intracardiac procedures which may be used for treatment of PFO.

Although available devices may work well in some cases, they also face a number of challenges. Relatively frequent causes of complications include, for example, improper deployment, device embolization into the circulation and device breakage. In some instances, a deployed device does not heal into the septal wall completely, leaving an exposed tissue which may itself be a nidus for thrombus formation. Furthermore, currently available devices are generally complex and expensive to manufacture, making their use for prophylactic treatment of PFO and other defects impractical. Additionally, currently available devices typically close a PFO by placing material on either side of the tunnel of the PFO, compressing and opening the tunnel acutely, until blood clots on the devices and causes flow to stop.

Research into methods and compositions for tissue welding has been underway for many years. Of particular interest are technologies developed by McNally et al., (as shown in U.S. Pat. No. 6,391,049) and Fusion Medical (as shown in U.S. Pat. Nos. 5,156,613, 5,669,934, 5,824,015 and 5,931,165). These technologies all disclose energy delivery to tissue solders and patches to join tissue and form anastamoses between arteries, bowel, nerves, etc. Also of interest are a number of patents by inventor Sinofsky, relating to laser suturing of biological materials (e.g., U.S. Pat. Nos. 5,725, 522, 5,569,239, 5,540,677 and 5,071,417). None of these disclosures, however, show methods or apparatus suitable for positioning the tissues of an anatomic defect for welding or for delivering the energy to an anatomic defect to be welded.

Causing thermal trauma to a patent ovale has been described in two patent applications by Stambaugh et al. (PCT Publication Nos. WO 99/18870 and WO 99/18871). The devices and methods described, however, cause trauma to PFO tissues to hopefully eventually cause scar tissue formation which will close the PFO. In addition, Blaeser et al. (US Patent Publication US2003/0208232), further describes causing trauma, or abrading, and holding the abraded tissue in apposition to allow the tissue to heal together. Using such devices and methods, the PFO typically remains patent immediately after the procedure, or abrasion, and only closes sometime later, or is treated and then held together to heal over time. Frequently, scar tissue may fail to form or may form incompletely, resulting in a still patent PFO.

In addition to PFO, a number of other anatomic tissue defects, such as other ASDs, ventricular septal defects (VSDs), patent ductus arteriosis (PDA), aneurysms and other blood vessel wall defects, atrial appendages and other naturally occurring cavities within which clot can form, and the like cause a number of different health problems (note that the term "defect" may include a naturally occurring structure that results a potential health risk such as the clot forming in the atrial appendage). U.S. Patent Application No. 2004/0098031 (Van der Burg), and U.S. Pat. No. 6,375,668 (Gifford) and U.S. Pat. No. 6,730,108 (Van Tassel et al.), the full disclosures of which are incorporated herein by reference, disclose a variety of techniques and devices for treating anatomic defects. In addition, the inventors of the present invention have described a number of improved devices, methods and systems for treating PFO, many of which may be adapted for treating other anatomic tissue defects as well. For example, related patent applications assigned to the assignee of the present invention include U.S. patent application Ser. No. 10/679,245, filed Oct. 2, 2003; and Ser. No. 10/811,228, filed Mar. 26, 2004, and U.S. Pat. No. 7,165,552, filed on Sep. 16, 2003; and U.S. Pat. No. 7,186,251, filed Feb. 25, 2004, the full disclosures of which are incorporated herein by reference.

Despite improvements made thus far, it would be advantageous to have even further improved methods and apparatus for treating anatomic tissue defects such as PFOs and the other anatomic structures mentioned above. Ideally, such methods and apparatus would help seal an anatomic tissue defect during, immediately after or soon after performing a treatment procedure. Also, such devices and methods would leave no foreign material (or very little material) in a patient's heart. Furthermore, such methods and apparatus would preferably be relatively simple to manufacture and use, thus rendering prophylactic treatment of PFO and other tissue defects a viable option. In addition, based upon the unique characteristics of the devices of the present invention, such devices may also be employed for treating certain electrophysiological defects, such as atrial fibrillation, supraventricular tachacardia (SVT), atrial flutter, A-V node re-entry, and Wolf Parkinson White syndrome. At least some of these objectives will be met by the present invention.

BRIEF SUMMARY OF THE INVENTION

The present invention generally provides devices and methods for treating anatomic defects in human tissues, such as patent foramen ovale (PFO), atrial septal defect, ventricular septal defect, patent ductus arteriosis, left atrial appendages, and blood vessel wall defects. In one aspect of the present invention, a method of treating an anatomic defect in human tissue involves positioning a distal end of an elongate catheter device at the site of the anatomic defect, engaging tissues at the site of the anatomic defect to bring the tissues together, and applying energy to the tissues with the catheter device to substantially close the anatomic defect acutely. In another aspect of the present invention, the device can be positioned to apply energy at an appropriate tissue location, such as in the vicinity of the pulmonary vein, for treatment of atrial fibrillation. In various embodiments, the anatomic defect may be any suitable tissue defect, such as but not limited to those listed above. The following description will often focus on PFO treatment, but various embodiments may be employed for treating any other suitable tissue defect.

By "substantially," it is meant that a stable tissue bridge will be formed across the anatomic defect, which will withstand physiologic pressures. A substantially closed anatomic defect, however, may still have one or more small gaps or openings, which will in at least some cases close over time via the healing process. By "acutely," it is meant that the anatomic defect is substantially closed when the closure procedure is completed. Thus, acute closure distinguishes devices and methods of the present invention from prior protocols, which rely on delayed anatomic defect closure via tissue healing and scarring. "Acutely," for purposes of this application, does not mean temporarily, since devices and methods of the present invention will typically provide for permanent (or at least long-term) anatomic defect closure.

The phrase "tissues adjacent an anatomic defect," for the purposes of this application, means any tissues in, around or in the vicinity of an anatomic defect which may be used or manipulated to help close the anatomic defect, or decrease viability of tissue conduction, such as in ablation for electrophysiological defects. For example, tissues adjacent a PFO include septum primum tissue, septum secundum tissue, atrial septal tissue lateral to the septum primum or septum secundum, tissue within the tunnel of the PFO, tissue on the right atrial surface or the left atrial surface of the atrial septum and the like.

In various embodiments, any of a number of energy transfer devices and forms of energy may be used to provide energy transfer. Types of energy used may include, for example, radiofrequency energy, cryogenic energy, laser energy, ultrasound energy, resistive heat energy, microwave energy and the like. Application of energy to tissues to substantially close the anatomic defect acutely may sometimes be referred to as "tissue welding." Preferably, tissue welding methods of the present invention will be performed without using tissue soldering material or other foreign material. In some embodiments, however, it may be advantageous to use one or more solder materials. Various solders and other tissue soldering matrices are described more fully in U.S. patent application Ser. No. 10/665,974, which was previously incorporated by reference. Examples of tissue solders or adhesives which may be used include, but are not limited to, autologous blood, albumin, collagen, fibrin, cyanoacrylates, mussel byssus adhesives, polymer hot melt adhesives and the like.

In various embodiments, tissues may be brought together (or "apposed") before, during and/or after application or removal of energy to the tissues. Generally, energy application or removal will act to denature collagen in the anatomic defect tissues. If the tissues are apposed before and/or during denaturation and/or after denaturation, the collagen in once-separated tissues binds together to bring the tissues together. Therefore, various embodiments of the invention include one or more devices for bringing (and possibly holding) tissues together before, during and/or after energy application or removal. Such devices include, for example, tissue covering members, which may also be suction or vacuum application members, expandable members for insertion and expansion within an anatomic defect, distal tip members for contacting a left atrial surface of PFO tissue and the like.

In some embodiments, positioning the distal end of the catheter device comprises advancing the catheter device intravascularly over a guidewire extending through the anatomic defect. Sometimes, advancing the catheter device over the guidewire positions the distal end in a substantially centered position over the anatomic defect or region to be treated. The method may optionally also involve removing the guidewire from the anatomic defect after it is substantially closed. In some embodiments, the guidewire extends asymmetrically through the anatomic defect. In some embodiments, positioning the distal end further comprises expanding an expandable member on the guidewire to adjust the position of the guidewire relative to the anatomic defect. Alternatively, the guidewire may be removed prior to or during the treatment and the device held in position by using mechanical assistance such as tensioning wires or suction. In some embodiments, positioning further comprises steering the distal portion of the catheter device.

Optionally, the method may also include visualizing at least one of the distal portion and the anatomic defect during the positioning step. For example, visualizing may involve viewing the anatomic defect directly with an endoscopic device coupled with the catheter device. Alternatively, visualizing may involve viewing at least one radiopaque marker of material on the distal portion, using a radiographic visualization device or visualizing the device and defect via MRI, ultrasound techniques, such as intracardiac echocardiography (ICE) or transesophageal echo (TEE). Visualization can be used to ensure the appropriate placement or positioning of the device relative to the defect either instead of a guidewire or other steering device, or in conjunction with such access devices.

Either the positioning step or the engaging step of the method may involve forming a seal between the distal end and the tissues to be treated. In some embodiments, engaging the tissues at the site of the anatomic defect involves applying a vacuum force. Optionally, applying the vacuum force may involve collecting vacuum force in a reservoir coupled with the catheter and applying the collected vacuum force as an impulse to the tissues. The method may optionally further include passing fluid out of the distal end of the catheter device to provide irrigation and suctioning the fluid back into the catheter device using the applied vacuum to create a "closed loop" environment within which energy can be efficiently applied. In some embodiments, the suctioned fluid may be monitored to determine flow rate, or the amount of blood, thereby indicating whether a seal has been formed.

In another aspect of the present invention, a method of treating a patent foramen ovale in a heart involves positioning a distal end of an elongate catheter device adjacent the patent foramen ovale, engaging tissues adjacent the patent foramen ovale by applying a vacuum at a first pressure through the catheter device to bring the tissues together, and applying energy to the tissues with the catheter device to substantially close the patent foramen ovale acutely. Such a method may optionally further include passing fluid out of the distal end of the catheter device at a second pressure to contact the tissues, with the first pressure being sufficiently greater than the second pressure to hold the tissues together and draw the passed fluid back into a lumen of the catheter device. The method may also involve monitoring the fluid drawn back into the catheter device to determine if the fluid contains blood. The method may alternatively include monitoring the flow rate of the fluid out of a supply reservoir and into the catheter to detect changes in vacuum pressure of the system. This monitoring can be done by a flow rate indicator, or by the user visualizing graduation marks on the fluid reservoir and timing fluid withdrawal. Some embodiments include flushing the lumen and the distal end of the catheter device to prevent accumulation of blood therein. In some embodiments, applying the vacuum forms a seal between the distal end of the catheter device and the tissues.

In another aspect of the present invention, an apparatus for treating an anatomic defect in a heart includes an elongate catheter having a proximal end and a distal end, a vacuum application member coupled with the distal end for engaging tissues at the site of the anatomic defect and applying vacuum to the tissues to bring them together, and at least one energy transmission member coupled with the vacuum application member for applying energy to tissues at the site of the anatomic defect to substantially close the anatomic defect acutely.

In some embodiments, the elongate catheter is tapered from the proximal end to the distal end. The elongate catheter may include a reinforced proximal portion for enhancing pushability of the catheter. In some embodiments, a distal portion of the catheter is curved to facilitate positioning of the vacuum application member over the anatomic defect. In some embodiments, the vacuum application member is curved to facilitate its positioning over the anatomic defect.

In a number of embodiments, the vacuum application member comprises a housing coupled with the distal end of the elongate catheter. The housing may be coupled asymmetrically with the distal end, to facilitate positioning and/or engagement of the device with tissues. The housing may be made of any suitable material, such as but not limited to polymers and the like such as polyester (e.g., PET, DACRON® from E. I. Du Pont de Nemours and Company, Wilmington, Del.), polypropylene, PTFE, ePTFE, PEEK, nylon, polyurethane, polyethylene, silicone, urethane. The housing may also be made from a metal fabrication, such as a mesh, insulated by a polymer such as those listed above. In some embodiments, the housing comprises at least one supportive strut for preventing collapse of the housing when vacuum is applied to the tissues, and to allow torqueing of the housing for optimal positioning of the device. The strut may be a single wire-like structure, or a mesh or other reinforcing element. In some embodiments, the housing and the strut may comprise the same material. Alternatively, the housing and the strut may comprise different materials. The strut is designed to allow retraction of the housing into the catheter device.

In various embodiments, the housing may include any of a number of features for enhancing a tissue closure procedure. In some embodiments, for example, the housing comprises a plurality of ridges for preventing complete collapse of the housing when vacuum force is applied, while also facilitating flexibility to allow the housing to be retracted into the catheter device. To enhance visualization of the device, the housing may include at least one radiopaque marker and/or radiopaque material. In some embodiments, the housing includes a flexible, cylindrical foot at its distal-most end for contacting the tissues. The cylindrical foot, in some embodiments, may have a larger height at one side of the housing than at an opposite side of the housing. In one specific embodiment, for example, the larger height of the foot at one side is about 3 mm and the smaller height at the opposite side is about 1 mm.

As already mentioned, the energy applied or transmitted by the device may be any suitable form of energy in various embodiments, such as RF, microwave, cryogenic, ultrasound or any other suitable form of energy. The energy transmission member(s), therefore, may be any of a number of different suitable energy transmission devices. In one embodiment, the energy transmission member comprises a radiofrequency energy electrode. The electrode may comprise, for example, a planar surface electrode extending over a mouth of the vacuum application member. Such a planar surface electrode may comprise, for example, a mesh, a lattice, a wire, a patterned metallic surface or the like. In some embodiments, the planar surface electrode further includes at least one attachment member extending outward from the electrode to attach the electrode to the vacuum application member. Attachment members in one embodiment comprise a plurality of metallic prongs.

In some embodiments, the electrode further comprises at least one guidewire aperture to allow passage of a guidewire through the electrode. In some embodiments, the guidewire aperture is disposed along the electrode in an offset position to facilitate positioning of the electrode over the anatomic defect. In other embodiments, two offset guidewire apertures are included for facilitating positioning of the electrode over the anatomic defect. The guidewire aperture may be connected to a lumen, such as a hypotube to allow multiple guidewire passes through the device. Additionally, the aperture or lumen may be formed to direct the guidewire such that it exits the guidewire aperture in a predetermined trajectory. Optionally, a thermocouple may be attached to the electrode. In one embodiment, the electrode is constructed as one piece. In one embodiment, the electrode is flexible, foldable and retractable into the catheter device.

Some embodiments of the device further include a vacuum reservoir coupled with the proximal end of the catheter and in fluid communication with the vacuum application member for accumulating vacuum force. The apparatus may also include a fluid introduction lumen extending through the catheter for passing fluid from the distal end of the catheter to contact the tissues. Fluid may be conductive or insulative, depending on the desired tissue effect and the power delivered.

In another aspect of the present invention, apparatus for applying energy to tissues adjacent an anatomic defect in human tissue includes a patterned planar surface electrode and at least one attachment member extending from the electrode to couple the electrode to a catheter device. The electrode may comprise, for example, a flexible metallic disk or the like. The disk may comprise a mesh, a lattice, a wire, a patterned metallic surface or the like. In one embodiment, the attachment members comprise a plurality of metallic prongs. Generally, the electrode may include any of the features described above.

These and other embodiments are described in further detail in the following description related to the appended drawing figures.

BRIEF DESCRIPTION OF THE DRAWING FIGURES

FIG. 2E is a side view of a catheter apparatus according to an embodiment of the present invention showing a curved reinforced catheter shaft;

FIG. 2F is a side view of a catheter apparatus according to an embodiment of the present invention, showing the distal portion having an electrode and an electrode housing having struts;

Figures 3, 3A, 3B:
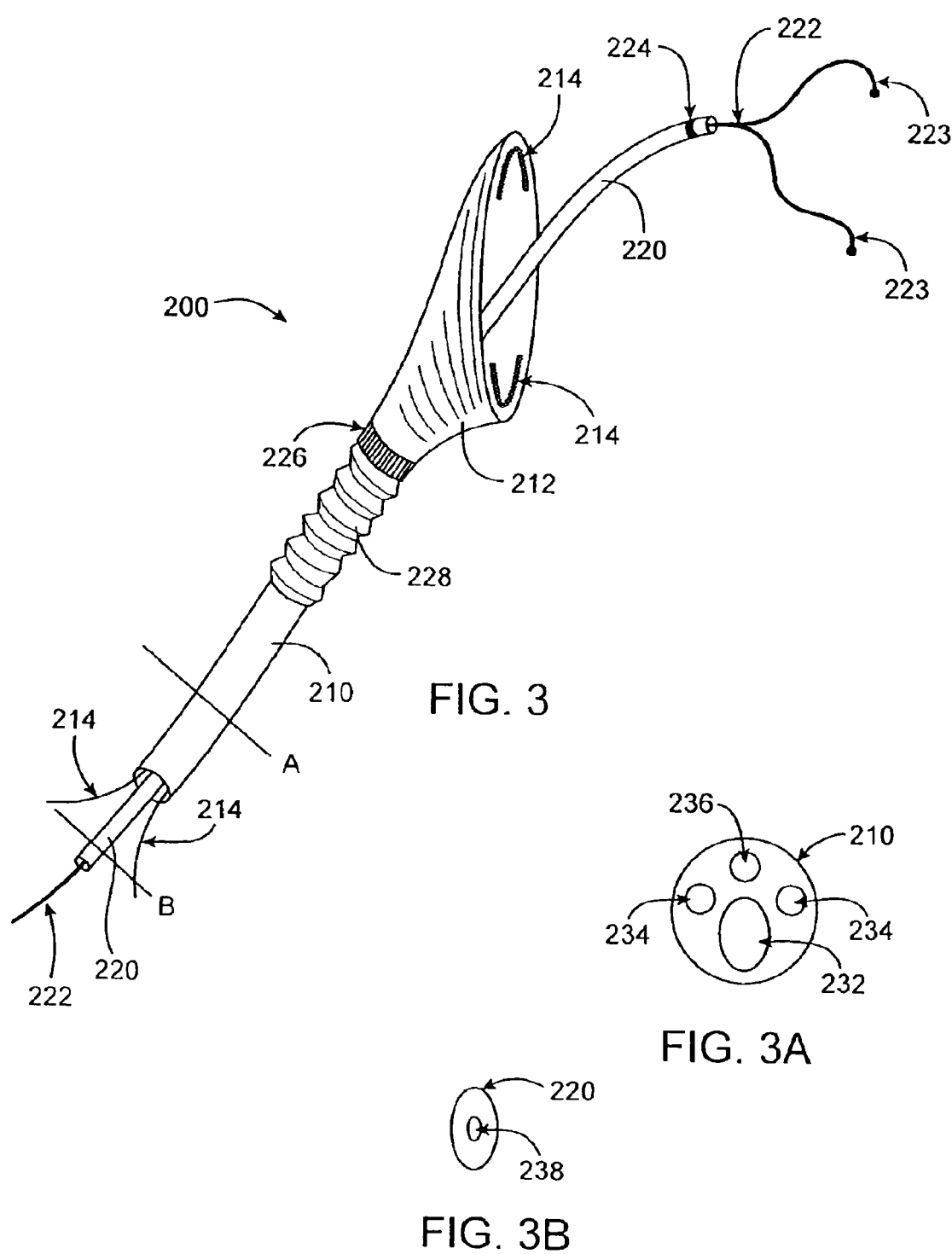
Figure 4:
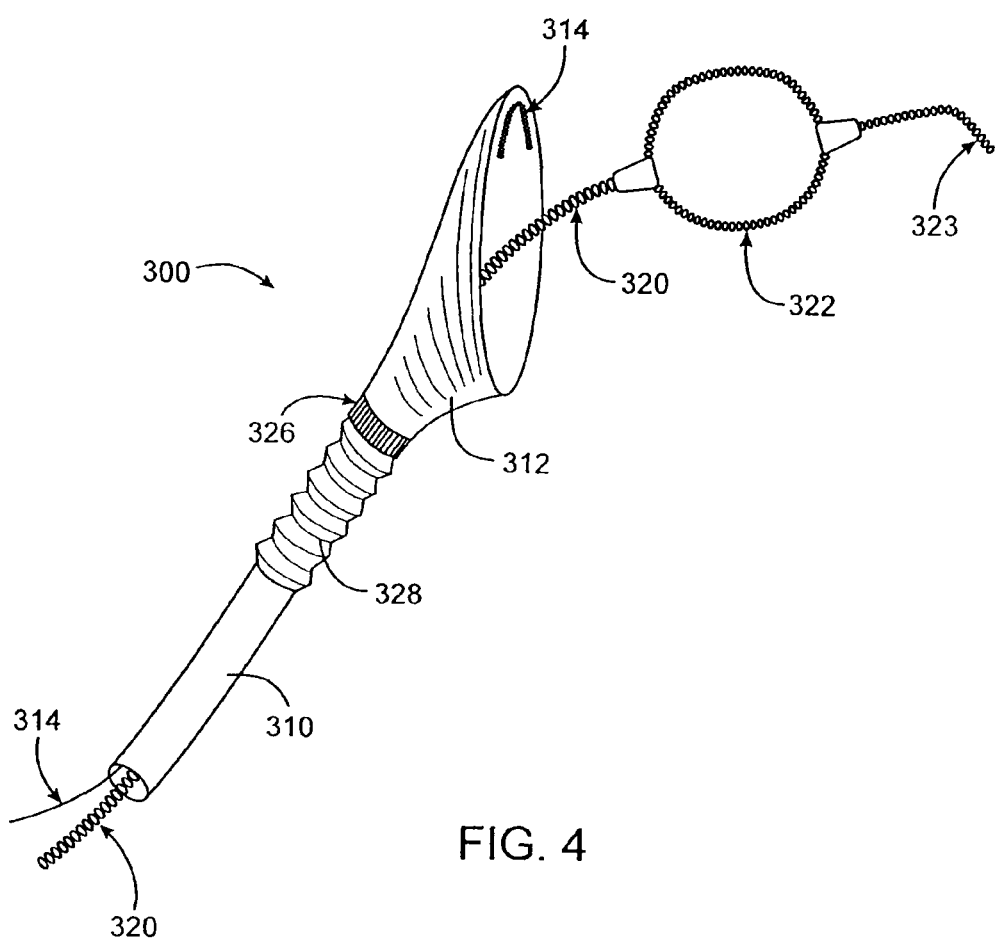
Figure 5:
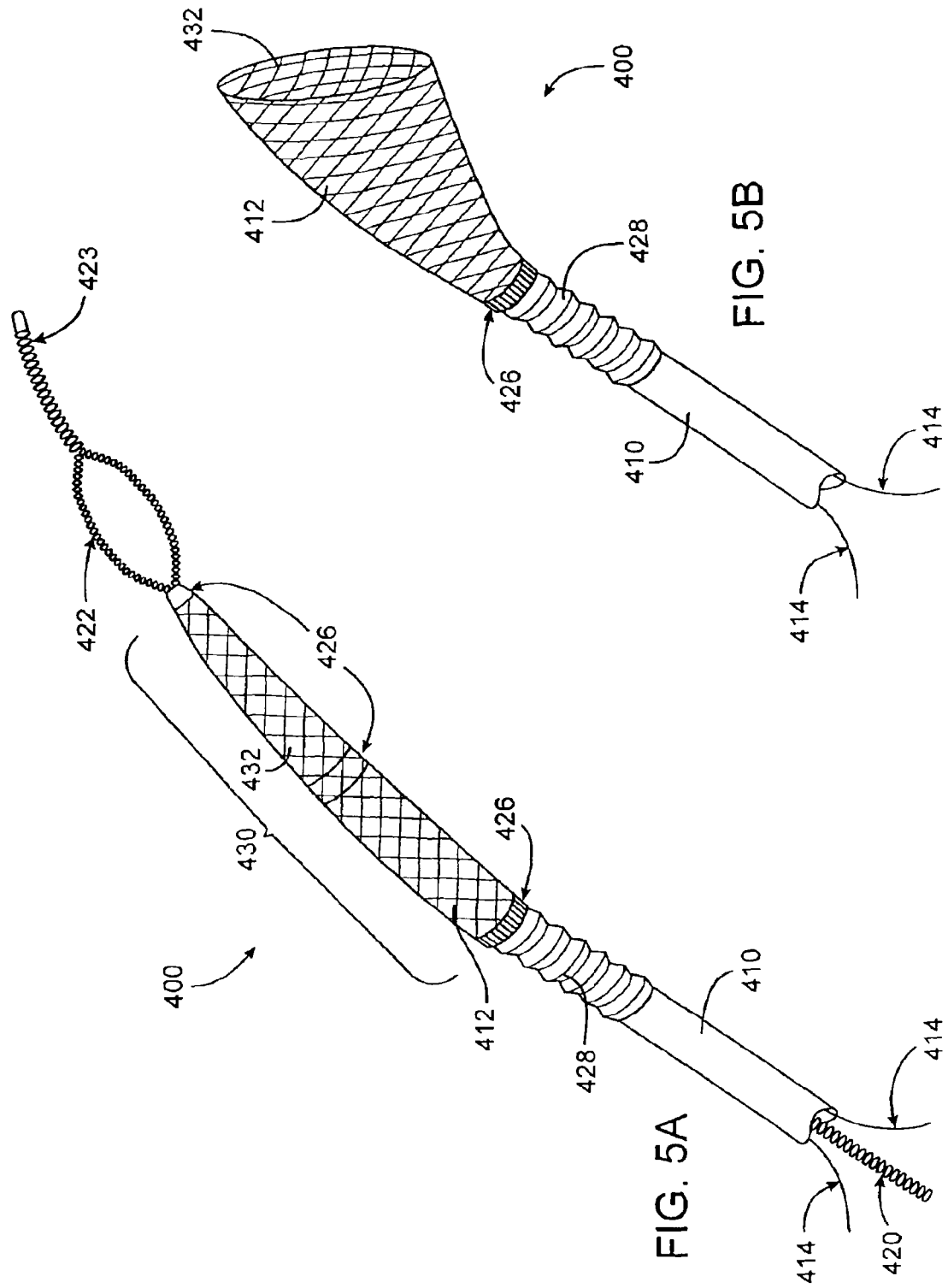
Figure 6:
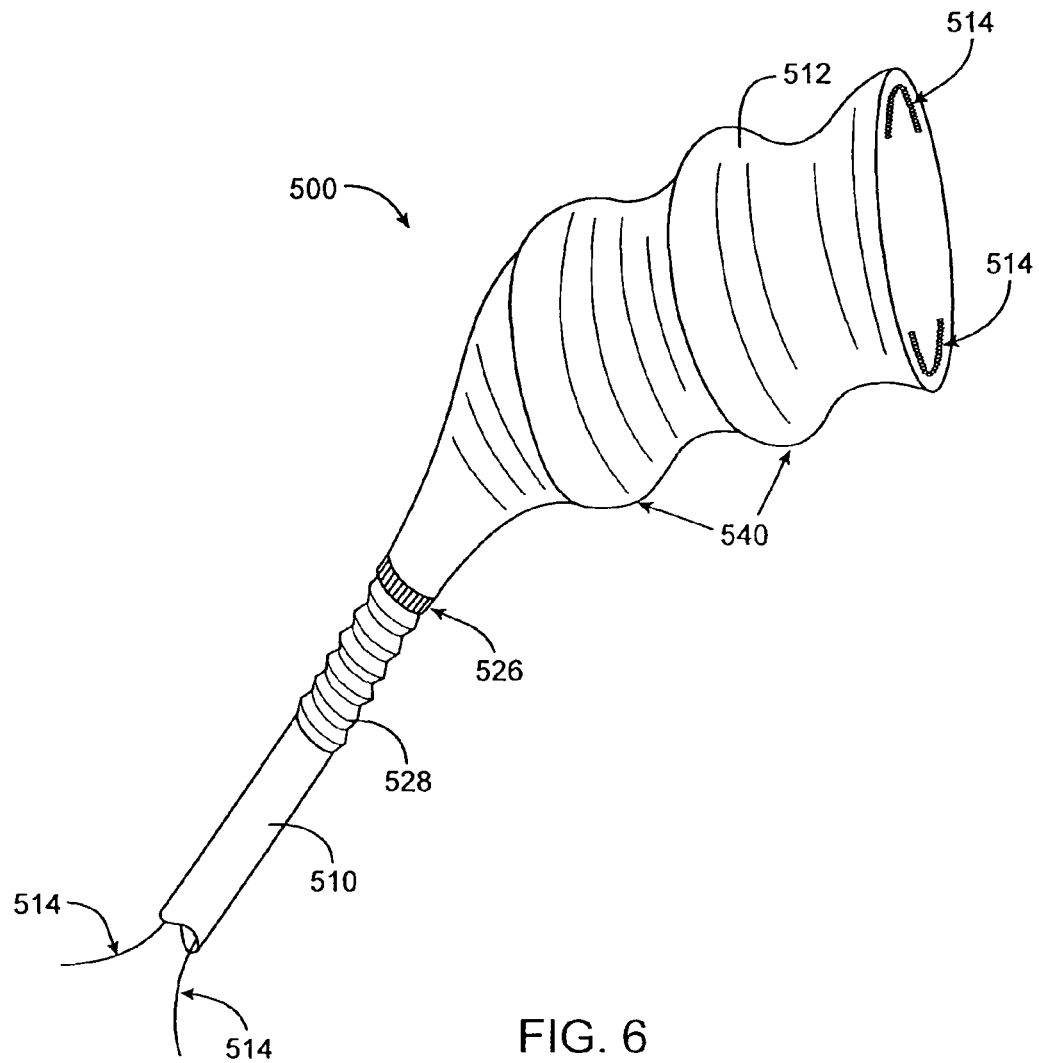
Figure 7:
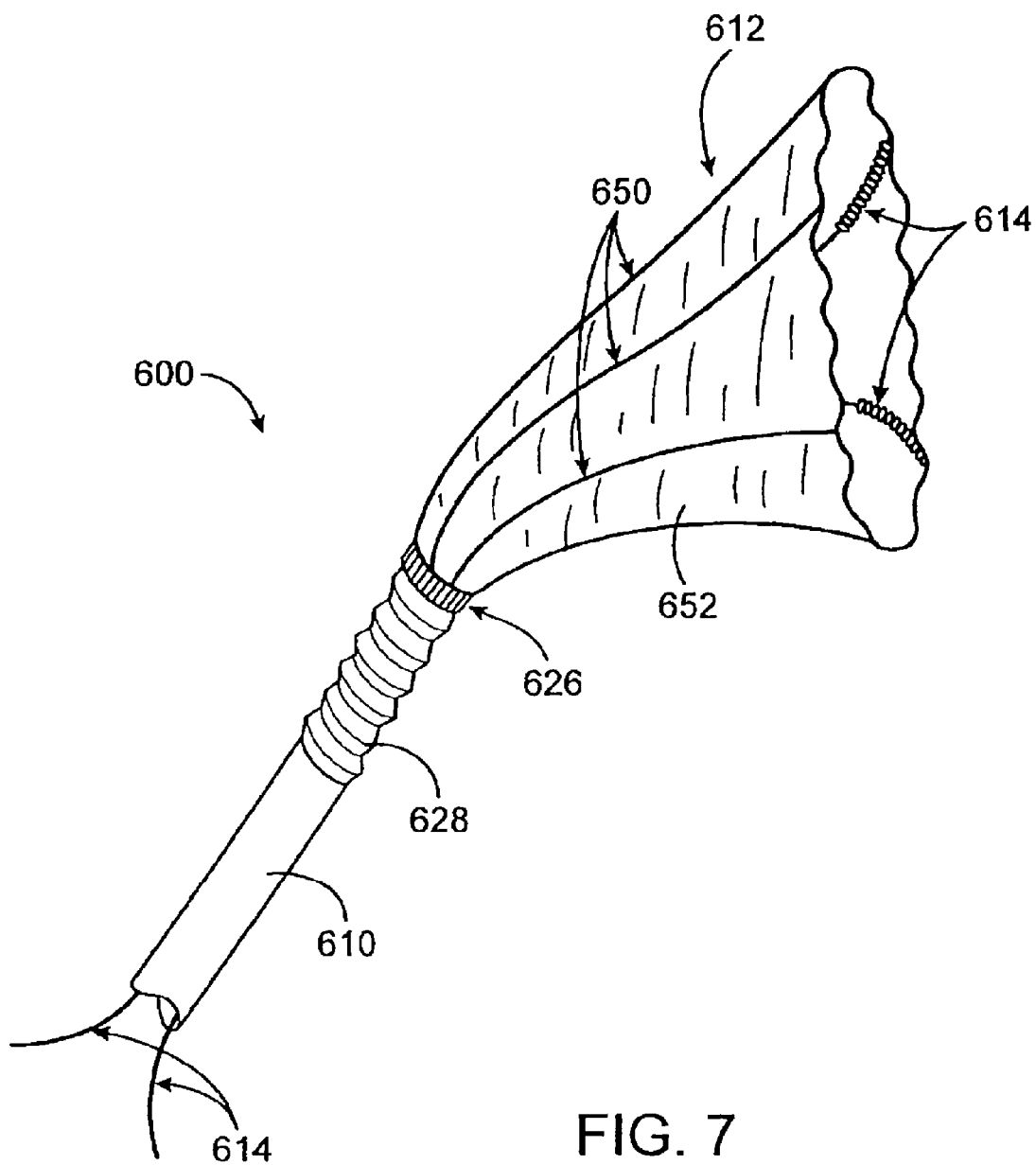

FIGS. 2G', 2G" and 2G"A show front, back and end-on views, respectively, of the electrode housing;

FIG. 3 is a perspective view of a catheter apparatus according to an embodiment of the present invention;

FIGS. 3A and 3B are cross-sectional views of the catheter apparatus in FIG. 3;

FIG. 4 is a perspective view of a catheter apparatus according to another embodiment of the present invention;

FIGS. 5A and 5B are perspective views of a catheter apparatus according to another embodiment of the present invention;

FIG. 6 is a perspective view of a catheter apparatus according to another embodiment of the present invention;

FIG. 7 is a perspective view of a catheter apparatus according to another embodiment of the present invention;

FIGS. 8A-8E demonstrate a method for treating a PFO using a catheter apparatus according to an embodiment of the present invention; and FIGS. 9A-9E demonstrate a method for treating a PFO using a catheter apparatus according to an embodiment of the present invention.

DETAILED DESCRIPTION OF THE INVENTION

Devices and methods of the present invention generally provide for treatment of anatomic defects in human tissue, such as patent foramen ovale (PFO), atrial septal defect, ventricular septal defect, left atrial appendage, patent ductus arteriosis, vessel wall defects and/or the like through application of energy. In addition, electrophysiological defects, such as atrial fibrillation, supraventricular tachacardia (SVT), atrial flutter, A-V node re-entry, and Wolf Parkinson White syndrome, may be treated with devices and methods of the present invention. The following descriptions and the referenced drawing figures focus primarily on treatment of PFO, however any other suitable tissue defects, such as but not limited to those just listed, may be treated with various embodiments of the invention.

Figure 1:
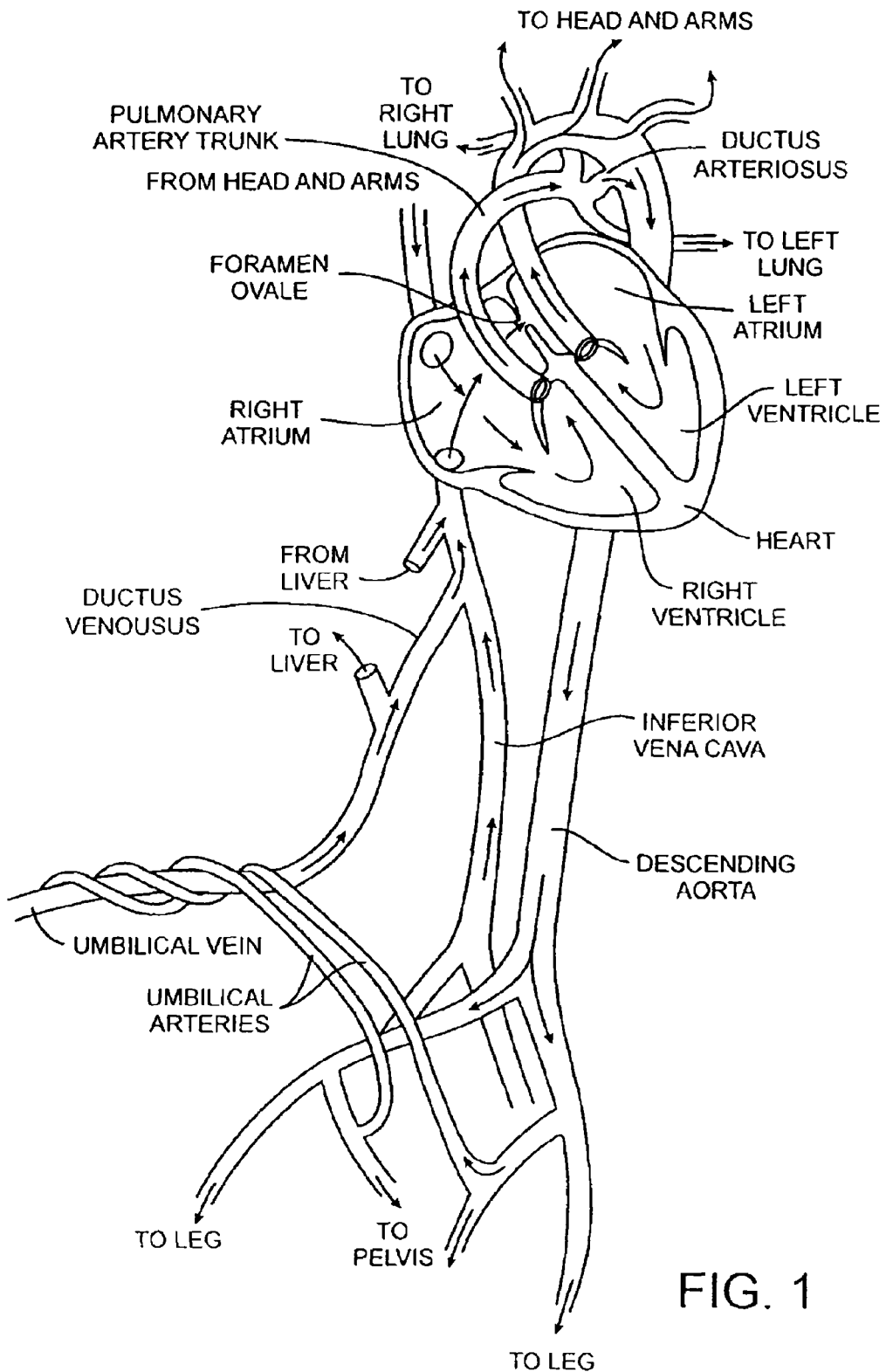
FIG. 1 is a diagram of the fetal circulation.

As mentioned above in the background section, FIG. 1 is a diagram of the fetal circulation. The foramen ovale is shown, with an arrow demonstrating that blood passes from the right atrium to the left atrium in the fetus. After birth, if the foramen ovale fails to close (thus becoming a PFO), blood may travel from the right atrium to the left atrium or vice versa, causing increased risk of stroke, migraine and possibly other adverse health conditions, as discussed above.

I. Catheter Device

Figure 2:
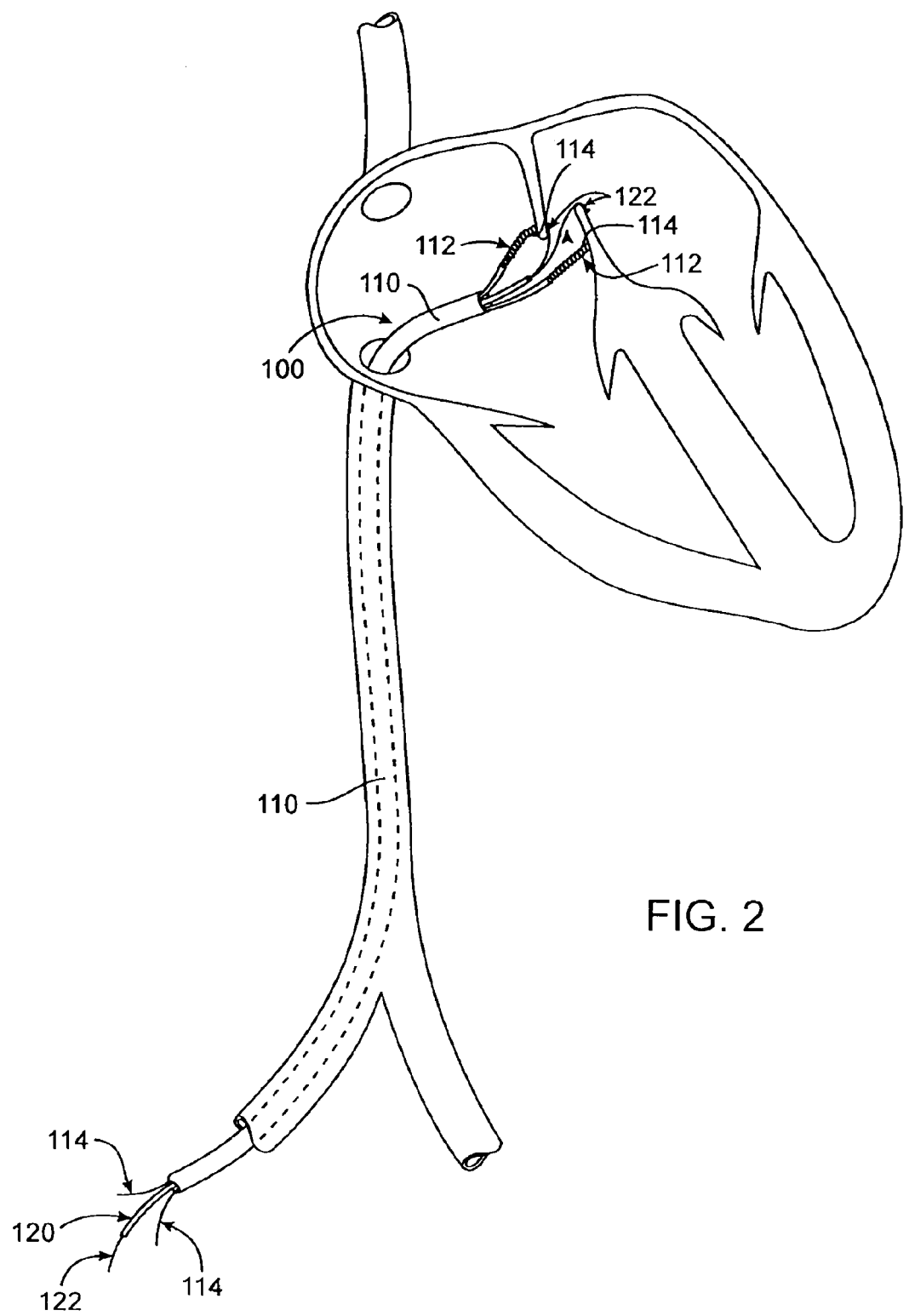
FIG. 2 is a diagram of a catheter apparatus according to an embodiment of the present invention, having a conductive element and closure device, the catheter passing through the inferior vena cava and right atrium and through the defect, exemplified as a PFO.

With reference to FIG. 2, one embodiment of a defect treatment device, depicted as a PFO-treatment apparatus 100 may be advanced through the vasculature of a patient to a position in the heart for treating a PFO. In this embodiment, apparatus 100 includes an elongate catheter device 110 having one or more tissue apposition members 112 and one or more energy transmission members 114 at or near its distal end. Optionally, catheter device 110 may be slidably disposed over a guide member 120, such as a guide catheter (as in FIG. 2), a guidewire, or the like. Guide member 120 may include, for example, one or more expanding members 122 or other similar devices for deploying within the PFO to help appose the adjacent tissues. In some embodiments, as described further below, expanding members 122 may comprise (or be coupled with) one or more energy transmission members 114. Generally, apparatus 100 may be used to bring together tissues surrounding and/or adjacent the defect and transmit energy to the tissues to close or treat the defect.

Although the embodiment in FIG. 2 and many of the embodiments described below include one or more tissue apposition members 112, devices of the present invention do not require such members. In some embodiments, as mentioned above and as set forth in the claims, devices may include a catheter device having one or more energy transmission members 114 for applying or removing energy, without any components designed for bringing the tissues together. Therefore, although much of the following discussion focuses on embodiments including tissue apposition members and the like, such members are not required.

Figure 2A:
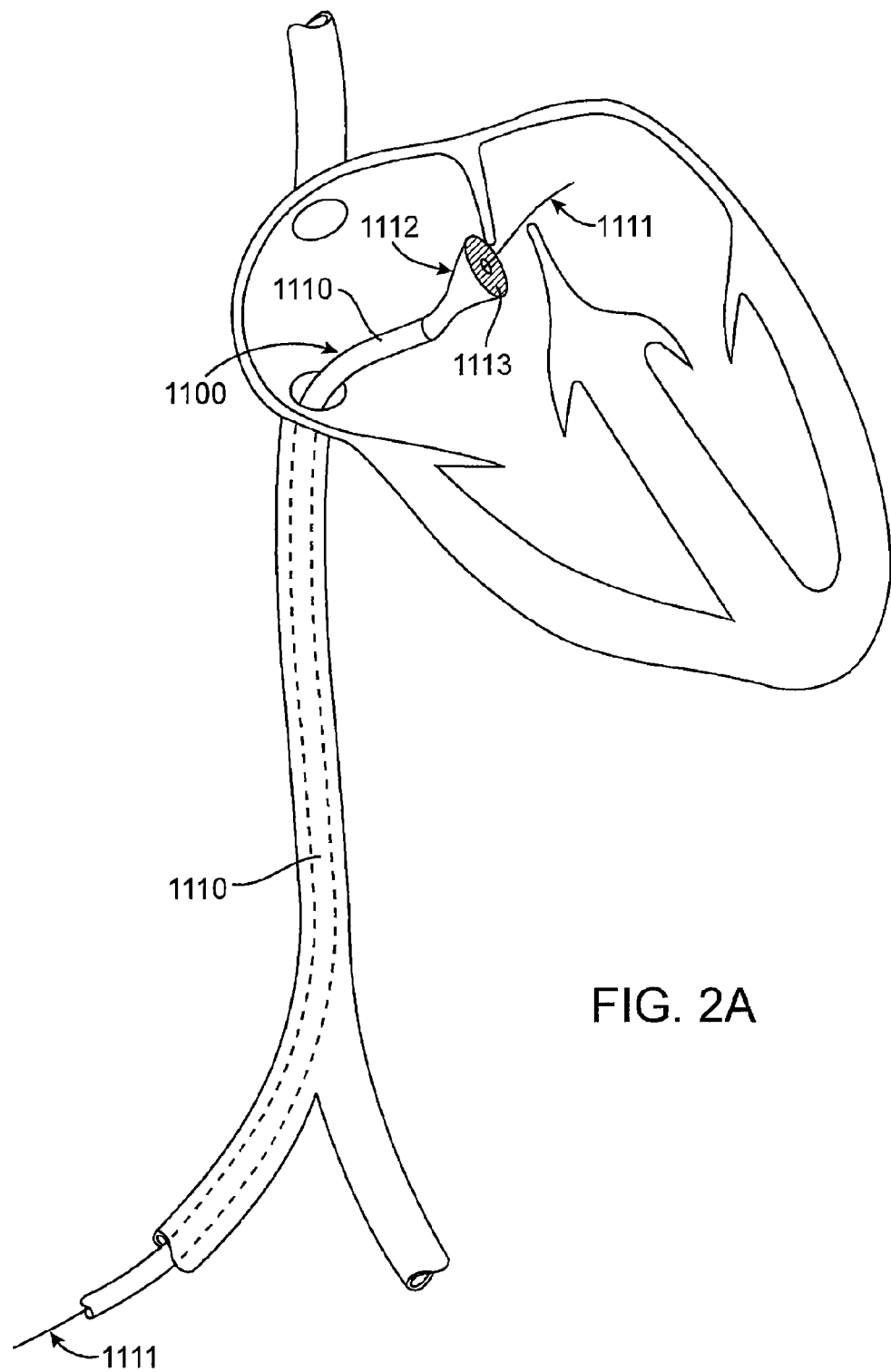
FIG. 2A is a diagram of a catheter apparatus according to an embodiment of the present invention, having an energy transmission member and a vacuum application member, the catheter passing through the inferior vena cava and right atrium and through the PFO.
Figure 2B:
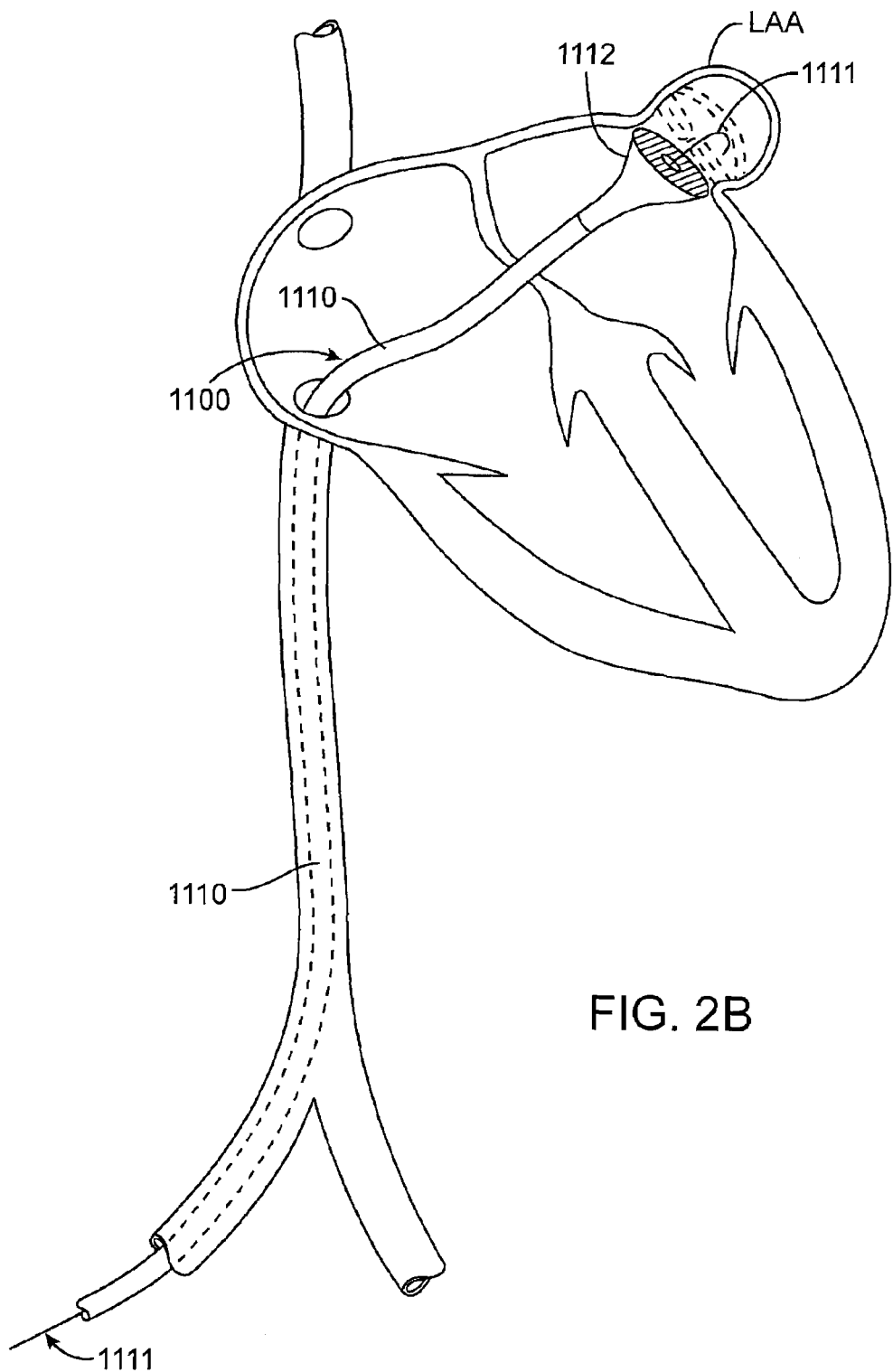
FIG. 2B is a diagram of a catheter apparatus according to an embodiment of the present invention, having an energy transmission member and a vacuum application member, the catheter passing through the inferior vena cava and transeptally into the left atrium and to the mouth of a left atrial appendage (LAA)

Referring now to FIG. 2A, another embodiment of an anatomic defect treatment apparatus 1100 is shown. Treatment apparatus 1100 generally includes a catheter body 1110, a vacuum application member 1112 and one or more energy transmission members 1113. Apparatus 1100 may be advanced over a guidewire 1111 extending through a PFO or other tissue defect. Energy transmission member 1113 comprises a planar, metallic electrode disposed within or near the distal end of the vacuum member 1112, as will be described in further detail below in reference to FIGS. 2C through 2G. FIG. 2B shows apparatus 1100, including a catheter body 1110, vacuum application member 1112 advanced over a guidewire 1111 and to the mouth of a defect, here a left atrial appendage (LAA). In operation, vacuum may then be applied to approximate the tissue at the mouth of the LAA and seal or flatten the defect (shown in dotted lines) and trap any clot residing therein, to prevent it from embolizing. The vacuum may cause the mouth of the LAA to close, or it may cause the LAA to empty and lay flat, approximating one edge of the mouth to the tissue on the opposite inner wall of the LAA (also shown in dotted lines), or it may approximate tissue in some other geometry.

Referring now to FIG. 3, another embodiment of a treatment apparatus 200 suitably includes a catheter device 210 coupled with a tissue apposition member 212 at its distal end. One or more energy transmission members 214 may be disposed through or within catheter device 210 and/or coupled with tissue apposition member 212. In some embodiments, catheter device 210 is slidably disposed over a guide catheter 220. Guide catheter 220 may contain one or more expandable elements 222, such as a guide wire or the like. One or more radiopaque markers 224, 226 may be included on catheter device 210, guide catheter 220 or both. Catheter device 210 may also include an isolation portion 228 for helping to stabilize tissue apposition member 212 during use, so that it is not caused to move due to the flexibility of catheter device 210.

FIGS. 3A and 3B show cross-sectional views of apparatus 200 from the perspective of lines A and B in FIG. 3, respectively. In FIG. 3A, catheter device 210 is shown, having a guide catheter lumen 232, two energy transmission member lumens 234 and a vacuum lumen 236. As shown in FIG. 3B, guide catheter 220 includes an expandable element lumen 238. Guide catheter lumen 232 may sometimes be configured with an inner diameter (or "profile") that is shaped (or "keyed") to allow guide catheter 220 to pass easily through lumen 232. This feature is demonstrated in FIGS. 3A and 3B, where guide catheter 220 and guide catheter lumen 232 each have an ovoid shape.

In general, catheter device 210 comprises an elongate, flexible catheter which may be advanced through the vasculature of a patient to a position in the heart for treating a defect. Thus, catheter device 210 may have any suitable length, diameter, cross-sectional profile and the like, and may be constructed of any suitable material. Tissue apposition member 212 (or multiple tissue apposition members in some embodiments) is disposed at or near the distal end of catheter device 210. Although many different types of devices may be used to bring tissues of the defect together, in one embodiment (shown in FIG. 2) tissue apposition member 212 comprises a defect covering member. Defect-covering tissue apposition member 212 may be positioned to contact adjacent PFO tissues to fully cover, or block, the opening of the defect. In the case of treating a PFO, this blocking of the PFO may prevent right-to-left shunting of blood and may allow blood pressure in the left atrium to bring the septum primum and septum secundum at least partially together to close the PFO. Therefore, simply by forming a seal or blockage over the PFO, tissue apposition member 212 may help bring the PFO tissues together to assist in PFO closure.

II. Tissue Apposition/Positioning

To optimize use, the device of the present invention is typically positioned so as to best treat the defect tissue. In addition, the device typically apposes or approximates the tissue to be treated to allow a "weld" or fusion to occur. Such positioning and tissue apposition may be achieved in a variety of ways, including those described herein. In the embodiment shown in FIG. 3, tissue apposition member 212, especially when configured as a PFO-covering member, may be collapsible/expandable to facilitate advancement and delivery of catheter device 210. For example, tissue apposition member 212 may comprise a collapsible polymeric cover disposed over an expandable/collapsible frame. In other embodiments, tissue apposition member 212 may be constructed of a shape memory material, such as Nitinol or another shape memory metal, spring stainless steel or the like, to allow catheter device 210 to be delivered through vasculature and then allow tissue apposition member 212 to expand to contact and appose the PFO tissues. In some embodiments, catheter device 210 and tissue apposition member 212 may be delivered to a location for PFO treatment through an introducer sheath. To further enhance the use of apparatus 200, an angle between catheter device 210 and tissue apposition member 212 may be selected to approximate a convenient angle for delivery and/or deployment. In one embodiment, for example, the angle between catheter device 210 and tissue apposition member 212 may approximate the angle between the inferior vena cava and the interatrial septum. Any other configuration, combination of angles and the like is contemplated, however. In some embodiments, for example, direct steering of the angle of tissue apposition member 212 relative to catheter device 210 may be employed to enhance delivery of catheter device 210 to a treatment site.

In this and other embodiments, tissue apposition member 212 may also include one or more vacuum members for applying vacuum to the defect tissues or those surrounding the defect. In one embodiment, for example, suction lumen 236 (FIG. 3A) may extend from the proximal end to the distal end of catheter device 210, opening into one or more vacuum-application apertures at the distal end of tissue apposition member 212. The vacuum-application aperture(s) may have any suitable configuration, such as a continuous aperture encircling tissue apposition member 212, multiple apertures encircling tissue apposition member 212 or in any other suitable configuration at or near its distal end, or the like. In still another embodiment, vacuum may be applied via a large, central lumen in tissue apposition member 212. In any case, vacuum force may be used to bring tissues together and/or to secure tissue apposition member 212 and thus catheter device 210 to the tissues.

To further facilitate use and positioning of apparatus 200, catheter device 210 may include one or more radiopaque markers 226 for facilitating visualization of the device 210. Catheter device 210 may also include a "flexible isolation portion" 228, which in some embodiments comprises a rigid but shapeable portion disposed toward the distal end of catheter device 210, between tissue apposition member 212 and the generally flexible proximal portion of catheter device 210. Flexible isolation portion 228 may help to isolate tissue apposition member 212 from some or all movement experienced by the more flexible, proximal portion of catheter device 210, thus allowing a PFO treatment procedure to be performed without significant movement of tissue apposition member 212. In other embodiments, flexible isolation portion 228 may be more flexible than the more proximal portion of catheter device 210, thus enhancing maneuverability, shapability or the like of the position of tissue apposition member 212 relative to the more proximal portion.

Figure 2C:
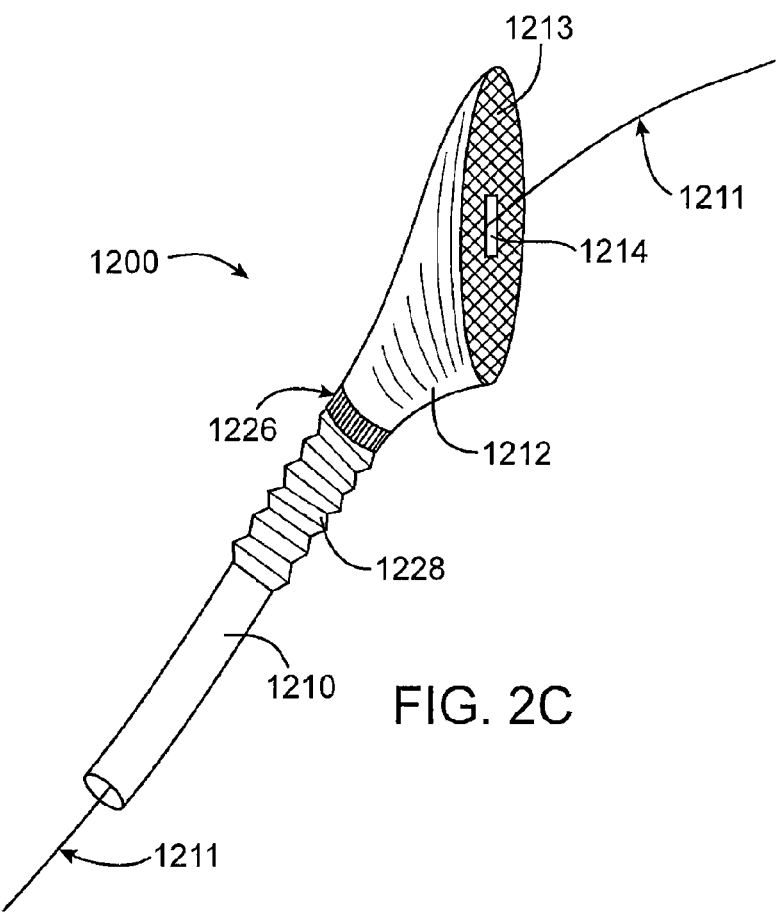
FIG. 2C is a perspective view of a catheter apparatus according to an embodiment of the present invention.
Figure 2D:
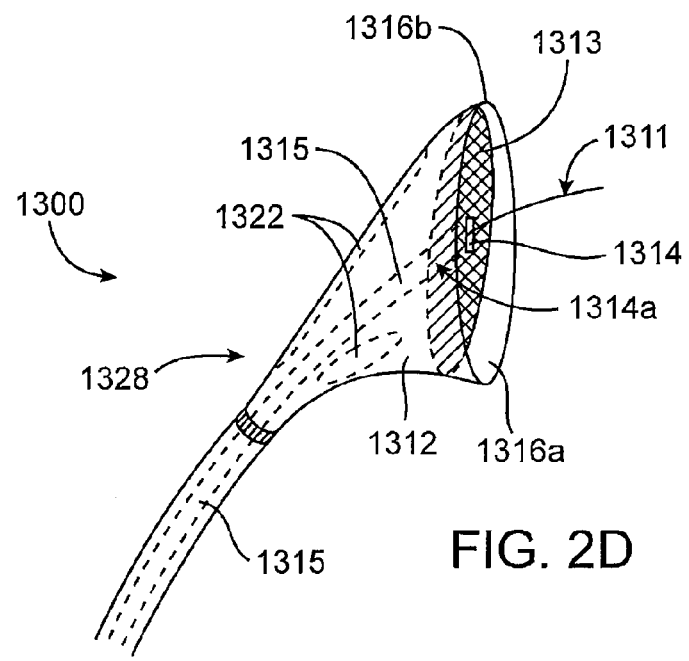
FIG. 2D is a perspective view of a distal end of a catheter apparatus according to an embodiment of the present invention.

Referring now to FIGS. 2C and 2D, distal portions of two embodiments of tissue treatment devices 1200, 1300 are shown. In FIG. 2C, treatment device 1200 includes a catheter body, having a neck 1228, shown here as flexible to allow deflection, or actively steerable and a radiopaque marker 1226. FIG. 2D depicts a neck 1328 that has a preformed bend. At the distal end of catheter body 1210 is attached a vacuum application member or housing 1212. At the distal end of housing 1212, a planar electrode 1213 for transmitting RF energy is disposed. The embodiment shown in FIG. 2D demonstrates several additional optional features of a tissue treatment device 1300, and in particular a tissue apposition member. In such an embodiment, a tissue apposition member may include a vacuum application housing 1312, for example, which may include multiple ribs 1322, ridges, grooves or the like, to provide support to vacuum housing, thus preventing its collapse when vacuum is applied. Vacuum housing 1312 itself may be made of any suitable material or combination of materials, such as but not limited to any suitable polymers. Ribs 1322 may be made of the same or different material as the rest of housing 1312, and are generally thickened or heightened portions of material. Additionally or alternatively, multiple struts 1317 (FIG. 2F) may be embedded within or attached to the wall of housing 1312 for providing similar support. Struts 1317 may also be separate from the housing and attached to the catheter shaft and electrode to allow for torque of the electrode itself. Alternatively, guidewire lumen 1315 as detailed below may serve a similar function, eliminating the need for strut elements. Grooves or valleys on the inner surface of housing 1312 between ribs 1322 may also enhance flow of substances, such as blood or infused fluid.

Referring to FIGS. 2D-2F, another optional feature of tissue apposition member of tissue treatment device 1300 includes a flexible foot 1316 at the distal end of vacuum housing 1312. In various embodiments, flexible foot 1316 may comprise simply an extension of the material of housing 1312, or in other embodiments it may comprise a different material. In some embodiments, foot 1316 is formed by recessing electrode 1313 within vacuum housing 1312. In one embodiment, foot 1316 comprises an asymmetric cylinder including a taller side 1316a and a shorter side 1316b. Such an asymmetric foot 1316 may facilitate creation of a seal between foot 1316 and tissues that are being brought together. Generally, foot 1316 is made of a flexible polymer such as those set forth above in this specification, or other material so as to promote engagement of foot 1316 with tissues while preventing unwanted tissue damage. Foot 1316 is also adapted to not roll in on itself when engaged with tissue, but to be conformable to the tissue to accommodate and seal over the geometry of the tissue defect which may include varying tissue depth or elevations, oddly shaped or sized perimeter, or multiple defects (such as in multiple flaps found in PFOs, or inhomogeneous tissue (e.g. thinner and thicker). Foot 1316 may be formed of a material such as silicone that can be molded such that the periphery of the foot cylinder may be thinner than the main body. Given the variability of certain defects and the desirability of having a catheter design that accommodates varying tissue geometry, it may be desirable to design the foot 1316 to expand or contract distance D as shown in FIG. 2F.

FIG. 2E further depicts the catheter 1300 and housing 1312. Catheter shaft 1310 may be formed of a braided construction to allow for kink resistance, pushability and torqueability of catheter shaft 1310 to the desired placement. To further facilitate placement and positioning of catheter shaft 1310, it may sometimes be desirable to torque the catheter from side to side and/or to advance the device over more than one guidewire. FIG. 2G' shows such an embodiment of a housing 1312 having multiple, asymmetric guidewire apertures 1314. Further, neck portion 1328 (FIG. 2E) may be preformed to have a radius of curvature (θ between a range of 0 to 90 degrees) to facilitate positioning of catheter 1300 over a tissue defect.

One or more structural elements, such as a strut 1317, a resilient mesh embedded in the housing and/or a torque cable or rod attached to the electrode, may be incorporated to allow the electrode and housing 1312 to be torqued and maneuvered. One such housing 1312 is further detailed in FIGS. 2F-2G", showing struts 1317 optionally embedded into housing material to provide control and rigidity to housing 1312 when shaft 1310 is torqued. Struts may extend the length of the catheter, or be terminated at the point of the radiopaque marker (RO) on the catheter shaft. In addition, struts may be truncated to only run a partial length of the housing as shown in FIG. 2G" 1350. In a further embodiment, strut may be a single element that is rigidly coupled to the electrode to assist in lowering the profile of the housing while still allowing torque of the electrode. In some embodiments it may be advantageous to fabricate the struts and the electrode as a one piece construction. Struts may further incorporate radiopaque markings 1340 to assist in visual orientation of the catheter under fluoroscopy, ultrasound, or other imaging modalities. Such markings 1340 as shown in FIG. 2G" may include an asymmetric component 1341 on the housing to assist the user in differentiating the right side from the left side of the catheter housing. Markings may be formed from techniques known in the art such as plating, use of metal markers such as tantalum, platinum, stainless steel, or imbuing contrast agents into the catheter material such as barium sulfate and the like. In some embodiments, the electrode and housing 1312 may be retracted into catheter sheath 1351 for introduction and removal of the device in a percutaneous manner. For example, in one embodiment a housing measuring about 0.50 inch in diameter may be retracted into or deployed from a shaft opening having a diameter of about 0.10 inch. In another embodiment for treating larger defects, the housing may measure about 1.0 inch and be capable of collapsing into a catheter shaft with a diameter of about 0.18 inch.

Returning to FIG. 3, some embodiments of apparatus 200 include guide catheter 220, or an alternative guide member as discussed further below. Guide catheter 220 is generally a flexible catheter along which catheter device 210 may be slidably advanced to a position for defect treatment. Guide catheter 210 is configured to fit at least partially within or against the defect, and optionally through the defect such as into the left atrium of the heart when treating a PFO. Optionally, one or more radiopaque markers 224 may be included on guide catheter.

Guide catheter 220 may contain one or more expandable members 222 or other similar devices for expanding within the defect to help bring the defect tissues together, anchor catheter device to the defect tissues, or both. As shown in FIG. 3, for example, a "fish mouth" or two-prong expandable member 222 may be deployed within a PFO. When the two arms of the fish mouth separate, PFO-adjacent tissues are stretched laterally such that they tend to come together in the middle. In some embodiments, expandable members 222 may assist in PFO tissue apposition either while extending into the left atrium, while in other embodiments expandable members 222 do not extend into the left atrium.

Expandable member 222 may have any suitable configuration and may be constructed from any suitable materials. For example, expandable member 222 may be spring loaded, made of shape memory material, such as Nitinol or spring stainless steel or the like. Alternatively, expandable member 222 may be expanded mechanically by one or more expansion members coupled with expandable member 222 and controlled via an actuator at the proximal end of guide catheter 220. During delivery of guide catheter 220, expandable member 222 resides within guide catheter 220. Guide catheter 220 may then be withdrawn to deploy expandable member 222 either within the defect or in the case of a PFO treatment, within the left atrium to be drawn back into the PFO. In some embodiments, expandable member 222 has one or more pre-shaped or shapeable distal tips 223. Tips 223 may be used, for example, to help locate and cross the defect. In the case of treating a PFO for example, tips 223 may also be used to contact a left atrial surface of the septum primum or other PFO tissue, so that when the expandable member 222 is pulled proximally tips 223 help bring the PFO tissues together and/or anchor apparatus 200.

In some embodiments, one or more expandable members 222 may include or be coupled with one or more energy transmission members. For example, expandable member 222 may include one or more radiofrequency transmission members for monopolar or bipolar RF transmission. A fish mouth expandable member 222, for example, may include a bipolar RF transmission member on each prong of the fish mouth. In some embodiments, energy transmission members may be included in or coupled with both expandable member 222 and tissue apposition member 212. In any such embodiments, some portions of the energy transmission member(s) may be insulated, to prevent unwanted energy transmission to tissues. For example, in some embodiments a distal tip extending to contact a left atrial surface of PFO tissues may be insulated to prevent energy transmission from the tip.

Referring now to FIG. 4, an alternative embodiment of a PFO-treatment apparatus 300 suitably includes a catheter device 310 having a tissue apposition member 312, radiopaque marker 326 and flexible isolation portion 328. For exemplary purposes only, this embodiment is shown having one energy transmission member 314, such as a monopolar RF transmission member. As shown, apparatus 300 may also include a guidewire 320, over which catheter device 310 may be advanced. Guidewire 320 includes a split, expandable portion 322, which may be released from catheter device 310 to expand within a PFO to bring PFO tissues together. Guidewire 320 also suitably includes a distal tip 323 for locating and crossing a PFO and/or for contacting a left atrial surface of the septum primum or other PFO tissue.

Apparatus 300 of FIG. 4 may include any of the features described above in relation to FIG. 3. In the embodiment in FIG. 4, apparatus 300 does not include a guide catheter, but instead includes guidewire 320. Guidewire 320 may serve many or all of the functions of the guide catheter and expanding member described above in reference to FIG. 3. Split portion 322 of guidewire 320 may be constructed of shape memory material or other suitable materials to allow it to expand when released from catheter device 310. Additionally, split portion 322 may include or be coupled with one or more energy transmission members instead of or in addition for energy transmission member(s) 314 coupled with tissue apposition member 312. Guidewire 320 may also include one or more distal tips 323, which again may be used to locate and cross a defect and/or to help appose defect tissues. In some embodiments, tip 323 may also include or be coupled with one or more energy transmission members.

Referring now to FIGS. 5A and 5B, another embodiment of a defect-treatment apparatus 400 suitably includes a catheter device 410 having a tissue apposition member 412, radiopaque markers 426 and flexible isolation portion 428. As shown, apparatus 400 may also include a guidewire 420, over which catheter device 410 may be advanced. Guidewire 420 includes a split, expandable portion 422, which may be released from catheter device 410 to expand within a defect to bring defect tissues together. Guidewire 420 also suitably includes a distal tip 423 for helping locate and cross the defect and/or for contacting a left atrial surface of the septum primum or other defect tissue to help bring the defect tissues together. In this embodiment, catheter device 410 also includes a braided portion 430 which includes the proximally-disposed tissue apposition member 412 and a more distal energy transmission portion 432, the latter of which is coupled with energy transmission members 414. Tissue apposition member 412 and energy transmission portion 432 may be a unitary braided member, with tissue apposition member 412 configured to cover energy transmission portion 432 in a retracted position and to provide vacuum force application.

In use, catheter device 410 is typically advanced over guidewire 420 to a treatment location. Split portion 422 and optionally distal tip 423 are then used to help appose the tissues adjacent the defect. Before, during or after retraction of guidewire 420, energy transmission portion 432 is retracted into tissue apposition member 412. Defect tissue is then brought together using tissue apposition member 412, and energy is transmitted to the tissues using energy transmission portion 432. In some embodiments, tissue apposition member 412 provides for application of vacuum energy to the tissues to suction the tissues at least partially into tissue apposition member 412, thus enhancing contact of the tissues with energy transmission portion 432. Energy transmission portion 432 may comprise, for example an electrode mesh material, while tissue apposition member 412 may comprise an elastic coated mesh or other material. Again, any features described above in reference to other embodiments may be applied to the embodiment shown in FIGS. 5A and 5B.

With reference now to FIG. 6, another embodiment of a defect-treatment apparatus 500 suitably includes a catheter device 510 having a tissue apposition member 512, energy transmission members 514, radiopaque marker 526 and flexible isolation portion 528. For simplicity, apparatus 500 is shown without a guide catheter or guidewire, though either may be included. In this embodiment, tissue apposition member 512 includes ribs or "bellows" 540 to facilitate placement and/or alignment of tissue apposition member 512 relative to the septal wall tissues to be treated and/or to enhance adherence of apparatus 500 to the septal wall. For example, ribs 540 may allow catheter device 510 to move somewhat freely relative to tissue apposition member 512, without displacing tissue apposition member 512 from the defect tissues.

Referring now to FIG. 7, another embodiment of a defect-treatment apparatus 600 suitably includes a catheter device 610 having a tissue apposition member 612, energy transmission members 614, radiopaque marker 626 and flexible isolation portion 628. Apparatus 600 is shown without a guide catheter or guidewire, though either may be included. In this embodiment, tissue apposition member 612 includes multiple struts 650 covered by a covering 652, which may comprise a polymeric covering or any other suitable material. Struts 650 may be self-expanding or may open via a mechanical opening actuator coupled with struts 650, such as opening apparatus used to open an umbrella. Energy transmission members 614 are coupled with self-expanding struts 650 on the internal surface of tissue apposition member 612, so as to contact defect tissue that is pulled within tissue apposition member 612, such as by applied vacuum force and/or by blood pressure from the left atrium.

III. Application of Energy

Generally, devices of the invention apply energy tissues using one or more energy transmission members (ETM). Such ETMs are typically described as electrodes, such as RF electrodes, for example as electrodes 214, 313, 314, 1213, 1313. In various embodiments, however, an ETM may comprise any of a number of devices and may transmit any suitable type of energy for closing an anatomic defect. Some types of energy which may be used, for example, include radiofrequency, cryogenic, resistive heat, ultrasound, microwave and laser energy. Radiofrequency ETMs may be either monopolar or bipolar, with monopolar catheter devices also including a grounding member. Energy transmission members may have any suitable configuration. For example, they may have a curved shape to approximate a radius of curvature of the defect, as shown in FIG. 3, or they may be configured as points for spot-welding the defect tissues, as a circular member for welding around the circumference of defect tissues, as one or more mesh or braided members disposed within the orifice of tissue apposition member 212 or the like. Furthermore, ETM may take the form of a planar electrode such as those shown in FIGS. 2D-2G". In some embodiments, ETMs are fixedly coupled with tissue apposition member 212, while in other embodiments ETMs are movable within tissue apposition member, for example to move about the circumference of the defect to weld defect tissues at multiple locations.

Referring again to FIGS. 2C and 2D, one form of ETM comprises a planar electrode 1313, which may have any suitable configuration and be made of any suitable material(s) in various embodiments. Electrode 1313 may also be attached to vacuum housing 1312 by any suitable means, such as adhesives, welding or the like. In one embodiment, electrode 1313 may include one or more attachment members, such as prongs or the like, which extend from the planar surface of electrode 1313 and are embedded in or attached to a surface of housing 1312. Planar electrode 1213 may comprise any suitable metallic material such as Nitinol, Elgiloy®, titanium, platinum, cobalt chromium, stainless steel or spring steel or other resilient material and be a wire mesh, a flexible circuit, a patterned metallic surface, or the like. Planar electrode 1213 may be formed from a single sheet, by being laser cut, photochemically etched, electron-discharge machined (EDM) or other useful processes known in the art. Furthermore, planar electrode 1213 may be plated or surface treated to be radiopaque and/or echogenic. Such plating may also allow for improved current conduction, and may be useful to create variable thickness electrodes that provide different current conductivity along the surface of one electrode. Platings or coatings may also serve as a "non-stick" surface to minimize tissue or blood debris from accumulating on the electrode.

Electrode 1213 also includes a guidewire port or ports 1214 for passage of a guidewire 1211. Guidewire port 1214 may be centrally located on the electrode face, or offset depending on the desired approach to the defect. The outlet of guidewire port 1214 may have a counter-bored, chamfered or rounded leading edge to provide for smooth guidewire passage. In various embodiments, electrode 1313 may have one or more than one guidewire port 1314. Is some cases, guidewire port 1314 is centered on electrode 1313, while in other embodiments, one or more guidewire ports 1314 may be located off-center on electrode 1313 as in FIG. 2C. Off-center or eccentric guide ports 1314 may facilitate localization and/or positioning of housing 1312 relative to a tissue defect such as a PFO, and may assist in the collapsibility of the housing 1312 for deployment purposes. Guidewire port 1314 may be an aperture in the electrode face, and may be further formed of a lumen or hypotube 1315 that extends into the catheter body to allow the operator to easily exchange guidewires, or insert guidewires at separate points during the procedure as desired. It may be desirable to form the guidewire port 1314 to include a ramp 1314a to predetermine the angle of outlet of the guidewire so that it exits at the desired trajectory. Alternatively, a guidewire 1311 with an expandable balloon may used and inflated within a tissue defect or beyond in the heart chamber (e.g. left atrium) to bias vacuum housing 1312 in a desired direction. It is also within the scope of the present invention to incorporate a balloon on the catheter shaft or guide to achieve a similar purpose.

FIG. 2G' further depicts a thermocouple (TC) and the electrical connection wire (EC) that can be fixed to the face of electrode 1313. Such connection may be integrally formed as part of the electrode fabrication (e.g. leaving material to form a landing site for the wires to be connected during electrode fabrication.) To accommodate all the functions described herein, catheter shaft 1310 includes one or more guidewire lumens 1342, an electrode lumen 1343, a thermocouple lumen, and an infusion port 1344. Vacuum may be applied through a separate lumen (not shown) or the annular space 1345 within the catheter body.

As mentioned earlier, the phrase "tissue welding" herein is used to mean application of energy to (or removal of energy from) defect tissues to substantially and acutely close the defect. Energy transmission members generally provide for transfer of energy to or from PFO tissues to denature collagen in the tissues, and when the collagen is allowed to renature, with the tissues apposed, the once separated tissues bind together to form a stable tissue bridge. This stable tissue bridge substantially and acutely closes the PFO, preferably permanently. PFO tissues may, in some embodiments, be brought and held together by one or more tissue apposition members 212. Energy transmission members provide sufficient energy transfer, for a sufficient time, to weld the tissues. The time span of energy transmission may be, for example, from about 0.5 seconds to about 15 minutes, and more preferably from about 30 seconds to about 5 minutes. Energy transmission, in some embodiments, may be from about 0.5 Watts to about 100 Watts, and more preferably from about 2 Watts to about 40 Watts. Any other suitable energy and timing combination may also be used. In one experimental example, a PFO in a section of pig heart tissue used ex-vivo in a flowing saline test fixture was closed by applying suction to appose the PFO tissues and applying RF energy at approximately 25 Watts for 7 minutes. RF energy application was then discontinued, but suction was continued for an additional 1 minute to keep tissues in apposition while the tissue cooled, to allow collagen in the tissues to reorganize and bind together to form a stable tissue bridge. Many other energy amounts, energy application times, tissue apposition times and the like are contemplated, however. Similarly, in the event that devices of the present invention are employed for ablation of EP defects, a variety of temperature, power and time combinations may be used.

Although any type of energy may be transmitted by ETMs, some embodiments will make use of monopolar or bipolar RF energy. Devices may use monopolar radiofrequency energy, for example, wherein energy is applied simultaneously to all conductive elements, completing the circuit through an external ground pad affixed to the skin of the patient. Alternatively, bipolar energy may be applied to all conductive elements simultaneously, and the circuit completed through a ground element incorporated elsewhere on apparatus 200. Further embodiments may include applying bipolar energy between two or more ETMs, which are electrically isolated from one another within catheter device 210.

Control systems coupled with ETM or tissue apposition member 212, or otherwise disposed within apparatus 200, may sense an amount of energy delivered to PFO tissues and, optionally, may automatically stop energy delivery upon detecting a change in condition of energy delivery, for instance an increase in electrical resistance or impedance or rate of change in impedance, in PFO tissues or in apparatus 200, an increased energy draw from the treatment apparatus, and/or the like. In some embodiments, energy delivery may be automatically stopped when an amount of delivered energy reaches a desired level, such as an amount of energy sufficient to substantially close the PFO. The amount of delivered energy may be monitored by any suitable method, such as monitoring temperature or impedance in PFO tissues or the like. In some embodiments, one or more sensors coupled with tissue apposition member 212, ETMs, or any other part of apparatus 200 may be used for monitoring such indicia. Examples of sensor devices include but are not limited to infrared sensing devices, thermistors and thermocouples. A control system may also include a microprocessor coupled with the sensors to determine when a desired amount of energy has been delivered and/or to automatically stop energy transmission. In alternative embodiments, a microprocessor may be included in apparatus 200 which can sense, monitor and control energy delivery, thus not requiring separate sensors.

IV. Method of Treatment

FIGS. 8A-8E demonstrate a method for treating a PFO according to one embodiment of the present invention. It should be emphasized that this is merely one possible embodiment, and that many alternative methods are contemplated. For example, steps may be modified, repeated, added or deleted from the method, the order of steps may be changed, and/or the like, without departing from the scope of the invention as defined by the appended claims. Therefore, the foregoing description should not be interpreted to limit the scope of the invention in any way.

Figure 8A:
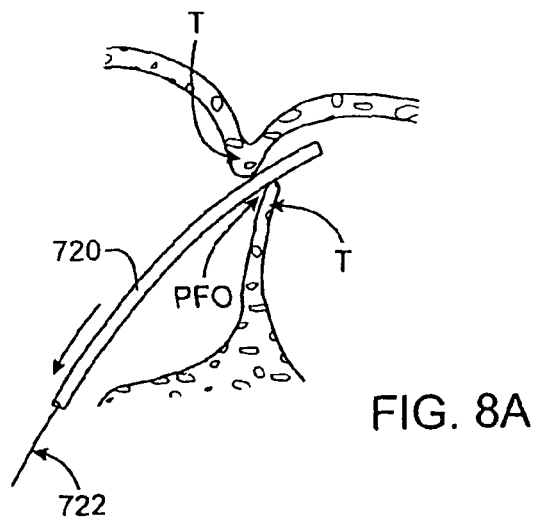
Figure 8B:
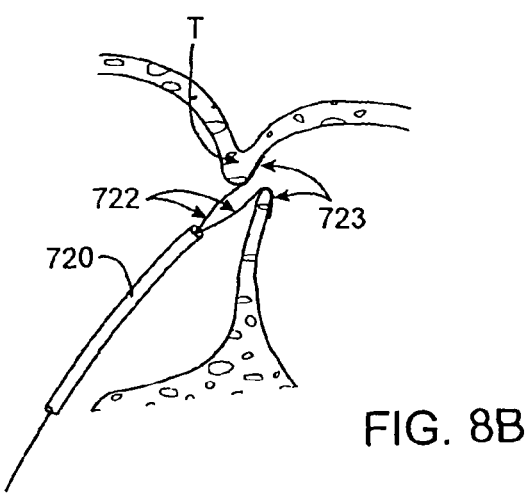

That being said, in one embodiment, a PFO treatment method includes advancing a guide catheter 720 through the PFO, between tissues T adjacent the PFO, the guide catheter 720 containing an expandable member 722 (FIG. 8A). Guide catheter 720 is then retracted (proximally pointing arrow) to expose expanding member 722 (FIG. 8B). Expanding member 722 may be exposed/expanded within the PFO, or may alternatively be exposed/expanded within the left atrium and pulled back into the tunnel of the PFO. Expanding member 722 may also include one or more distal tips 723, which may help to locate the PFO, cross the PFO, appose the tissues T and/or to anchor guide catheter 720 to the tissues T.

Figure 8C:
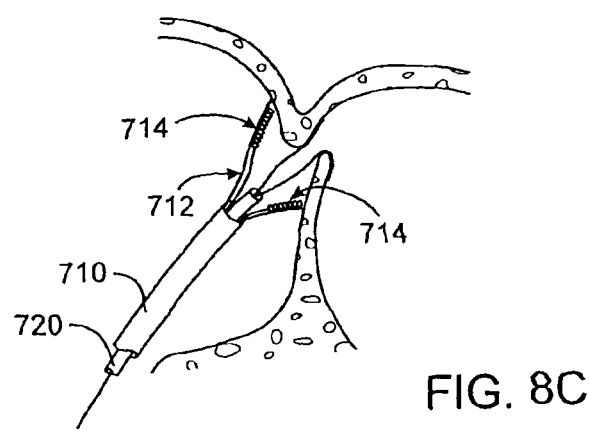
Figure 8D:
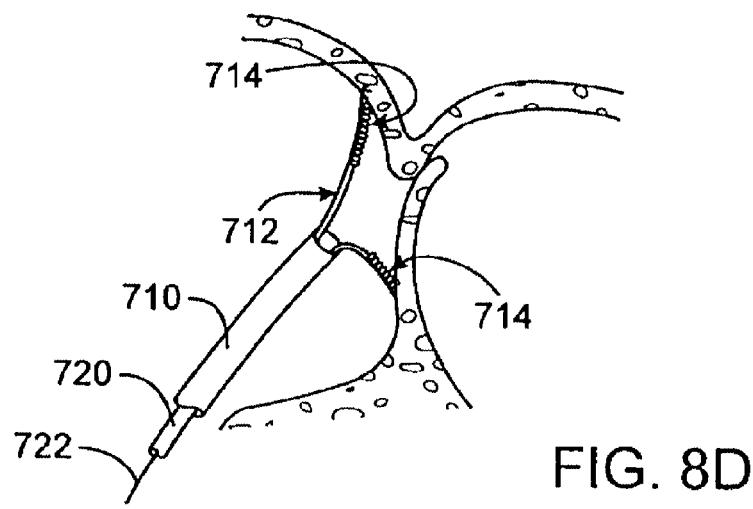
Figure 8E:
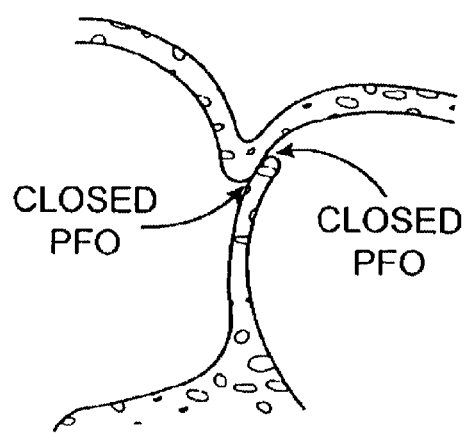

Once guide catheter 720 is in place and expandable member 722 is deployed, catheter device 710 may be advanced over guide catheter 720 to a position for treatment of the PFO (FIG. 8C). Catheter device 710 typically includes a tissue apposition member 712 (shown here in cross-section for clarity) and one or more energy transmission members 714. Suction may be applied using tissue apposition member 712, left atrial pressure may be used, or both, to bring tissues T adjacent the PFO together (FIG. 8D). Once tissue apposition member 712 is placed and/or activated, guide catheter 720 and expandable member 722 may be removed through catheter device 710, leaving the tissues T apposed and catheter device in place, as in FIG. 8D. Alternatively, guide catheter 720 and expandable member 722 may be left in place during a first welding to close the majority of the PFO and then removed. The small patent portions of the PFO remaining after the guide catheter 720 and expandable member 722 are removed may then be closed by a second weld or may be left open and allowed to close via healing or scarring. Tissue apposition member 712 may be used to hold tissues T together before, during and/or after energy transmission members 714 weld the tissues T together. Such holding of the tissues together and application of energy to weld the tissues may be performed for any suitable time, such as for less than one second to many minutes. Once a sufficient amount of energy has been applied to the tissues T to acutely close the PFO, catheter device 710 is removed, leaving a closed PFO, as in FIG. 8E.

Figure 9A:
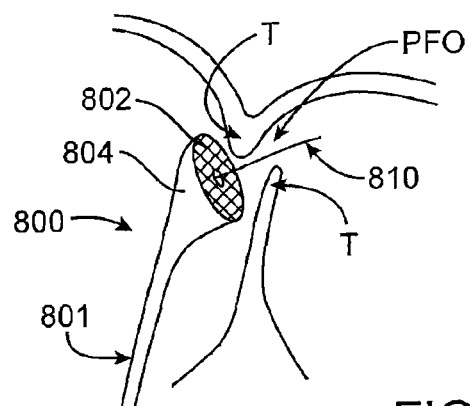

FIGS. 9A-9E demonstrate another embodiment of a method for treating a PFO. Such a method may also be used to treat other anatomic defects in human tissue, as discussed previously. In FIG. 9A, a tissue treatment device 800 including a catheter body 801, a vacuum application member 804 and an electrode 802 is advanced along a guidewire 810 to a position near tissues T adjacent the PFO. Using any of a number of different techniques, such as advancing device 800 over an eccentrically positioned guidewire 810, actively steering a distal end of device 800, visualizing device 800 using radiopaque markers and fluoroscopy or endoscopic devices such as flexible scopes, and/or the like, device 800 is generally positioned over the PFO.

Figure 9B:
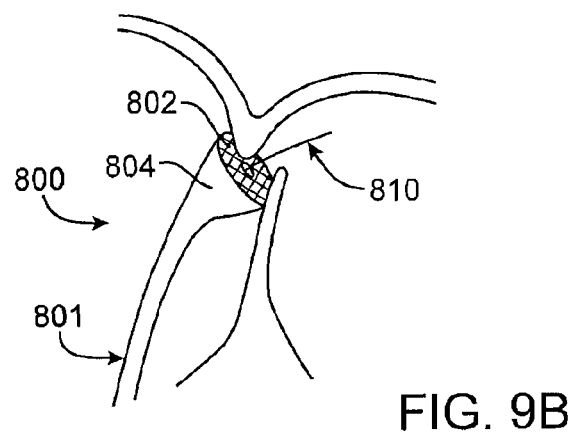
Figure 9C:
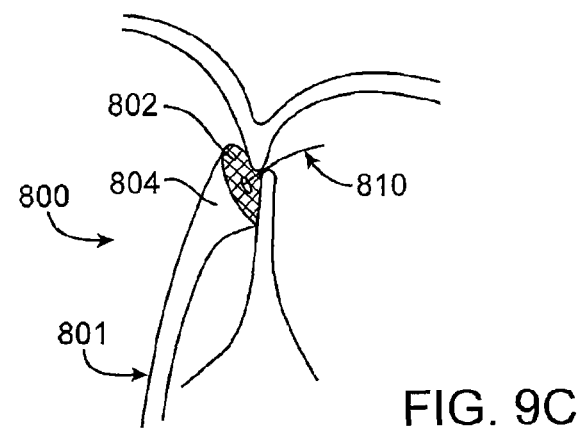

Next, as shown in FIG. 9B, device 800 is engaged with the PFO adjacent tissues T. A seal may be formed at this point between the distal end of device 800 and the tissues T. As shown in FIG. 9C, vacuum force may then be applied via vacuum application member 804, and energy may be applied to the tissues T via electrode 802. In some embodiments, vacuum force may first be stored in a reservoir and may then be applied to the tissues T as an impulse of vacuum to quickly form a seal and thereby minimize loss of blood from the patient. The vacuum force applied ensures that the flap of the defect furthest from the vacuum application member is snugly apposed with the flap nearest thereto. In addition, in cases where the defect is an opening and not a flap, applied vacuum force is typically sufficient to bring the tissues to be sealed in contact with each other. A number of PFO defects are accompanied by aneurysmal disease. In some embodiments, in addition to treating a PFO a method may also tighten or reinforce the septum of the heart, thus also treating the aneurysmal disease.

In some embodiments, irrigation fluid may be circulated through device 800 to irrigate the area of energy application to the tissues T. Such irrigation fluid may be circulated within vacuum housing 804, for example, by introducing fluid through a lumen of device 800 and then using the vacuum force to bring the fluid back into the lumen. In some instances, fluid flushing is used to prevent clotting and/or blood accumulation in housing 804. For this purpose a nonconductive fluid such as heparinized D5W may be used. In addition or alternatively, saline may be used to prevent clotting within the patient and/or device 800 (e.g., electrode housing, catheter lumen(s), or the like). Saline may also be employed to affect the heating characteristics of the desired treatment. Infusion may also act to cool the tissue interface, thereby preventing rapid tissue necrosis.

The procedure may be monitored in several ways. In some embodiments, the fluid brought back through the device is monitored for color, to determine when there is little or no blood in the fluid, thus helping to determine when a seal has been acquired and/or the PFO is closed. It may also be desirable to measure the impedance of the treatment region to determine if a seal is being maintained (impedance of blood is lower than tissue, so a change may indicate the presence of blood (leak) or lack of seal). Alternatively, an optical detector may be employed to control vacuum and shut off the force if blood is detected in the evacuated fluid. Similarly, the rate of extraction of fluid may be monitored and calculated to ensure that the rate of extraction equals that of infusion. In many cases, it may be sufficient to infuse fluid "passively" (from an IV fluid bag), e.g. gated by the rate of vacuum, to form a "closed loop" system where the rate of suction and aspiration maintain a seal on the defect site to allow the thermal energy treatment of the site. For safety purposes, a suction lock apparatus as is known in the art, may be employed on the proximal end of the catheter to ensure that fluid is not inadvertently extracted from the patient. Alternatively, the rate of extraction of the fluid from the supply reservoir (e.g. an IV bag) may be monitored to detect whether or not a seal against the tissue has been achieved. If a seal is achieved, the flow rate from the reservoir will increase. If a seal has not been achieved, or has been lost, passage of blood into the housing will predominate, slowing the flow rate from the reservoir.

Figure 9D:
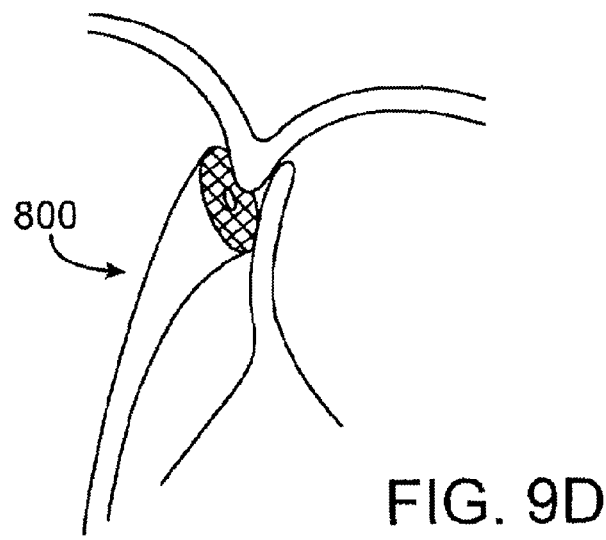
Figure 9E:
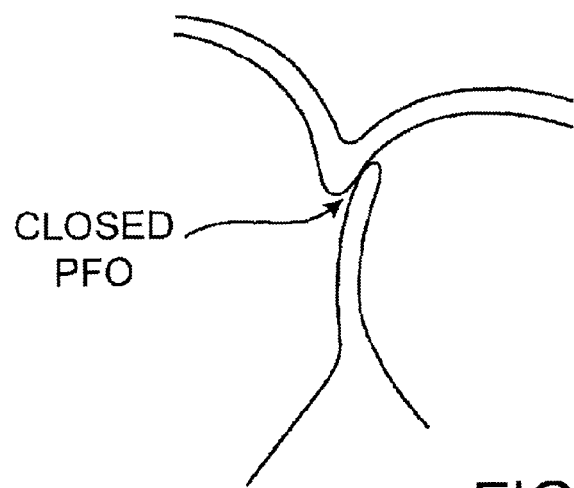

In FIG. 9D, the PFO has been closed and guidewire 810 has been withdrawn. In some embodiments, guidewire 810 is withdrawn after energy is applied and the PFO is closed, thus leaving a small hole in the closed PFO where guidewire 810 used to reside. Nevertheless, the PFO is still substantially closed, and the small hole left by guidewire 810 will typically close naturally, due to scarring. Finally, in FIG. 9E, device 800 is removed, leaving a substantially closed PFO. After the defect is closed, it may be desirable to maintain apposition of the defect tissue while tissue cools back down to body temperature, although this is not necessarily required for effective tissue bonding. In addition, it is within the scope of the invention to perform multiple applications of the energy device to treat the defect. This can be particularly advantageous with larger defects, or defects that present varied tissue thicknesses. Also contemplated by the present invention is the use of the device multiple times, or re-treating a defect that may re-cannulate following the initial treatment at a time period separate from the initial treatment.

The foregoing devices are particularly appropriate for welding of tissues where a device can be applied against two layers of tissue with or without suction as described above. However, some tissue defects, such as ASDs, VSDs, and similar defects, have a hole which must be closed. This means that the tissue must first be drawn into apposition either by vacuum or mechanical approximation before applying energy to weld those tissues together. One device which would be effective in drawing the tissues surrounding such an opening together was described in U.S. patent application Ser. No. 10/811,228 filed Mar. 26, 2004, which was previously incorporated by reference. This device described a tubular expandable clip with multiple distal-facing tines, mounted around an expandable tubular balloon. The balloon could be positioned in the defect and inflated until the balloon diameter is as large as the defect, while the clip and tines are proximal to the defect. The balloon and clip could then be advanced through the defect until the tines of the clip pierce the tissue surrounding the defect. The balloon could then be deflated, causing the clip to also contract radially, gathering the tissues together. Energy would then be applied to the tissue, either using the clip itself as the electrode, or an electrode on the surface of the balloon, or an entirely separate electrode. This energy would serve to weld the tissues in their gathered state. After welding, the balloon and clip could be withdrawn from the tissue, leaving the welded defect with little or no residual opening. This is only one exemplary device which could be used to draw the tissue surrounding an opening in a tissue structure together in order for the purpose of welding the tissue together. A PDA might also be closed using the balloon device described in the material incorporated immediately above, which would gather the tissue of the walls of the PDA together before applying energy.

As mentioned above, the foregoing method may be altered in any number of ways without departing from the scope of the invention. In some embodiments, for example, tissues adjacent the defect are brought at least partially together and energy is applied to the tissues to acutely close the defect with fewer steps and/or fewer device components than just described. For example, application of suction to appose tissues is not required in all embodiments. Furthermore, a variety of different types of energy may be applied to the tissues from a variety of differently configured energy transmission devices. In some embodiments, one or more of the steps described above may be repeated one or more times, such as by repeating a tissue welding step. The above description, therefore, is provided for exemplary purposes only.

Although the foregoing description is complete and accurate, it has described only exemplary embodiments of the invention. Various changes, additions, deletions and the like may be made to one or more embodiments of the invention without departing from the scope of the invention. Additionally, different elements of the invention could be combined to achieve any of the effects described above. Thus, the description above is provided for exemplary purposes only and should not be interpreted to limit the scope of the invention as set forth in the following claims.

What is claimed is:

1. A method for treating an electrophysiological defect in human tissue, the method comprising:
   positioning a tip end of a distal end of an elongate catheter device at a site of the electrophysiological defect, the positioning the tip end of the distal end including
      advancing the catheter device intravascularly over a guidewire extending adjacent to the electrophysiological defect, and
      engaging tissues by forming a seal between an opening of the tip end of the distal end of the elongate catheter device and the tissues at the site of the electrophysiological defect with the catheter device;
   applying energy to the tissues with the catheter device to substantially reduce the electrophysiological defect; and
   retracting an energy transmission member of the catheter device within the tip end of the distal end of the elongate catheter device.

2. The method as in claim 1, wherein the electrophysiological defect comprises one of atrial fibrillation, supraventricular tachycardia, atrial flutter, A-V node re-entry and Wolf Parkinson White Syndrome.

3. The method as in claim 1, wherein the tissues are in a vicinity of a pulmonary vein.

4. The method as in claim 1, wherein advancing the catheter device over the guidewire positions the tip end of the distal end in a centered position over the electrophysiological defect.

5. The method as in claim 1, further comprising removing the guidewire from the site of the electrophysiological defect after applying energy thereto.

6. The method as in claim 1, wherein positioning the tip end of the distal end further includes extending the guidewire asymmetrically through the site of the electrophysiological defect.

7. The method as in claim 1, wherein positioning the tip end of the distal end further comprises expanding an expandable member on the guidewire to adjust a position of the guidewire relative to the site of the electrophysiological defect.

8. The method as in claim 1, wherein positioning further comprises actively steering the distal end of the catheter device.

9. The method as in claim 1, further comprising visualizing the distal end during the step of positioning.

10. The method as in claim 9, wherein visualizing comprises viewing at least one radiopaque marker of material on the distal end, using a radiographic visualization device.

11. The method as in claim 9, wherein visualizing comprises using a technique selected from the group consisting of transesophageal echocardiogram, intracardiac echocardiography, MRI, fluoroscopy, ultrasound and direct vision.

12. The method as in claim 1, wherein engaging the tissues comprises applying a vacuum force.

13. The method as in claim 12, wherein applying the vacuum force comprises:
   collecting vacuum force in a reservoir coupled with the catheter; and
   applying the collected vacuum force as an impulse to the tissues.

14. The method as in claim 12, further comprising:
   passing fluid out of the tip end of the distal end of the catheter device to provide irrigation; and
   suctioning the fluid back into the catheter device using the applied vacuum.

15. The method as in claim 14, further comprising monitoring the suctioned fluid to determine the blood content of the fluid.

16. The method as in claim 14, further comprising monitoring a flow rate of fluid from a fluid supply reservoir into the catheter to determine whether a seal has been formed.

17. The method as in claim 1, wherein the positioning the tip end of the distal end further includes widening a braided mesh portion of the distal end.

18. The method as in claim 1, wherein the energy is applied to the tissues via an energy transmission member of the catheter device after retraction of the energy transmission member.

* * * * *